United States Patent
Sun et al.

(10) Patent No.: US 11,561,166 B2
(45) Date of Patent: Jan. 24, 2023

(54) FOCUSING LINEAR MODEL CORRECTION AND LINEAR MODEL CORRECTION FOR MULTIVARIATE CALIBRATION MODEL MAINTENANCE

(71) Applicant: VIAVI Solutions Inc., San Jose, CA (US)

(72) Inventors: Lan Sun, Santa Rosa, CA (US); Changmeng Hsiung, Redwood City, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 49 days.

(21) Appl. No.: 17/249,572

(22) Filed: Mar. 5, 2021

(65) Prior Publication Data

US 2021/0208059 A1  Jul. 8, 2021

Related U.S. Application Data

(63) Continuation of application No. 16/032,978, filed on Jul. 11, 2018, now Pat. No. 10,969,331.

(51) Int. Cl.
   *G01N 21/27* (2006.01)
   *G06F 17/18* (2006.01)

(52) U.S. Cl.
   CPC ........... *G01N 21/274* (2013.01); *G06F 17/18* (2013.01); *G01N 2201/12753* (2013.01); *G01N 2201/12769* (2013.01); *G01N 2201/12784* (2013.01)

(58) Field of Classification Search
   CPC .............................. G01N 21/274; G06F 17/18
   See application file for complete search history.

(56) References Cited

U.S. PATENT DOCUMENTS

| 5,459,677 A | 10/1995 | Kowalski et al. |
| 10,429,240 B2 | 10/2019 | Hsiung et al. |

(Continued)

FOREIGN PATENT DOCUMENTS

| CN | 103854305 A | 6/2014 |
| CN | 104089911 A | 10/2014 |

(Continued)

OTHER PUBLICATIONS

Jerome et al., "A Review of Calibration Transfer Practices and Instrument Differences in Spectroscopy," Applied Spectroscopy, Oct. 2017, vol. 72 (3), pp. 340-365.

(Continued)

*Primary Examiner* — Bryan Bui
(74) *Attorney, Agent, or Firm* — Harrity & Harrity, LLP

(57) ABSTRACT

A device may obtain a master beta coefficient of a master calibration model associated with a master instrument. The master beta coefficient may be at a grid of a target instrument. The device may perform constrained optimization of an objective function, in accordance with a set of constraints, in order to determine a pair of transferred beta coefficients. The constrained optimization may be performed based on an initial pair of transferred beta coefficients, the master beta coefficient, and spectra associated with a scouting set. The device may determine, based on the pair of transferred beta coefficients, a transferred beta coefficient. The device may determine a final transferred beta coefficient based on a set of transferred beta coefficients including the transferred beta coefficient. The final transferred beta coefficient may be associated with generating a transferred calibration model, corresponding to the master calibration model, for use by the target instrument.

20 Claims, 23 Drawing Sheets

(56) References Cited

U.S. PATENT DOCUMENTS

| | | | | |
|---|---|---|---|---|
| 10,928,309 B2* | 2/2021 | Hsiung | ................ | G01J 3/0275 |
| 2015/0160121 A1* | 6/2015 | Ridder | ................ | A61B 5/4845 |
| | | | | 702/85 |
| 2018/0031421 A1* | 2/2018 | Hsiung | ................ | G01J 3/0297 |
| 2020/0018691 A1 | 1/2020 | Sun et al. | | |

FOREIGN PATENT DOCUMENTS

| | | |
|---|---|---|
| CN | 106769981 A | 5/2017 |
| CN | 107664532 A | 2/2018 |
| JP | H09152399 A | 6/1997 |
| JP | 2018059900 A | 4/2018 |

OTHER PUBLICATIONS

Boucher T., et al., "Proximal methods for calibration transfer: Proximal Methods for Calibration Transfer", Journal of Chemometrics, Apr. 1, 2017, vol. 31(4), pp. e2877, XP055746684.

Liu Y. et al., "Linear Model Correction: A Method for Transferring a Near-Infrared Multivariate Calibration Model Without Standard Samples," Spectrochimica Acta Part A: Molecular and BiomolecularSpectroscopy, 2016, vol. 169, pp. 197-201.

Partial European Search Report for Application No. EP19185599.8, dated Nov. 16, 2020, 12 pages.

Workman J.J., et al., "A Review of Calibration Transfer Practices and Instrument Differences in Spectroscopy", Applied Spectroscopy, Oct. 25, 2017, vol. 72(3), pp. 340-365, XP055746662.

\* cited by examiner

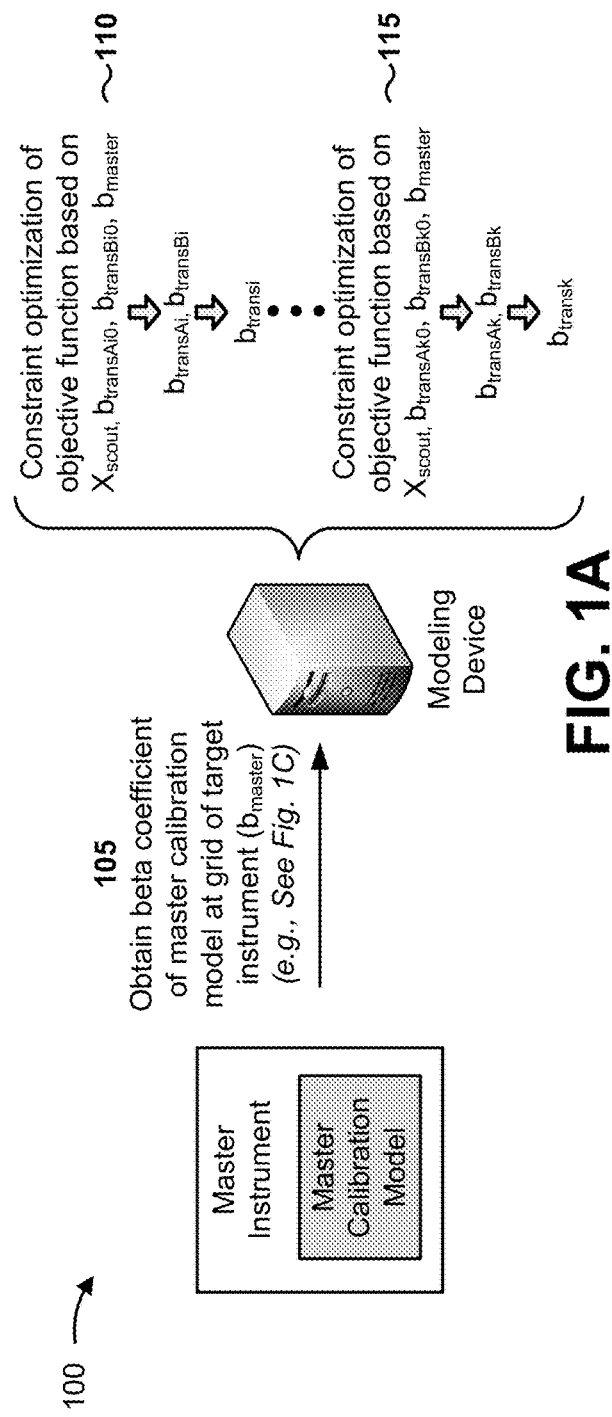
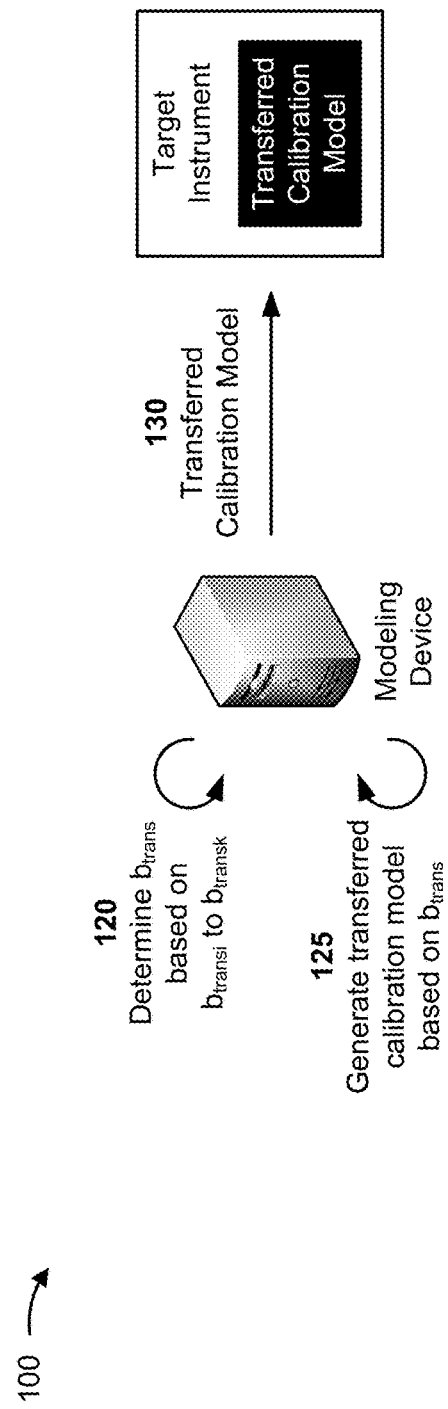

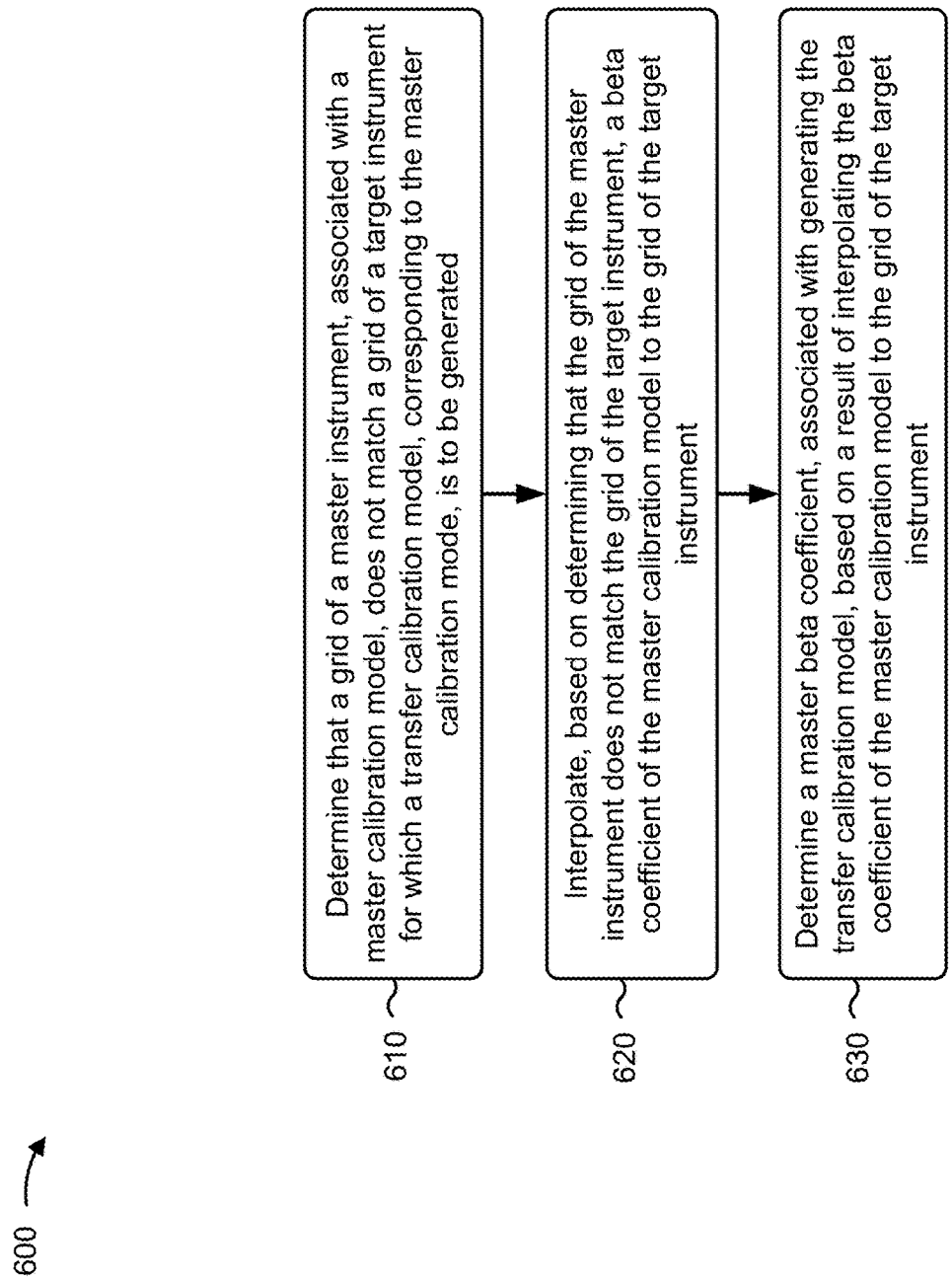

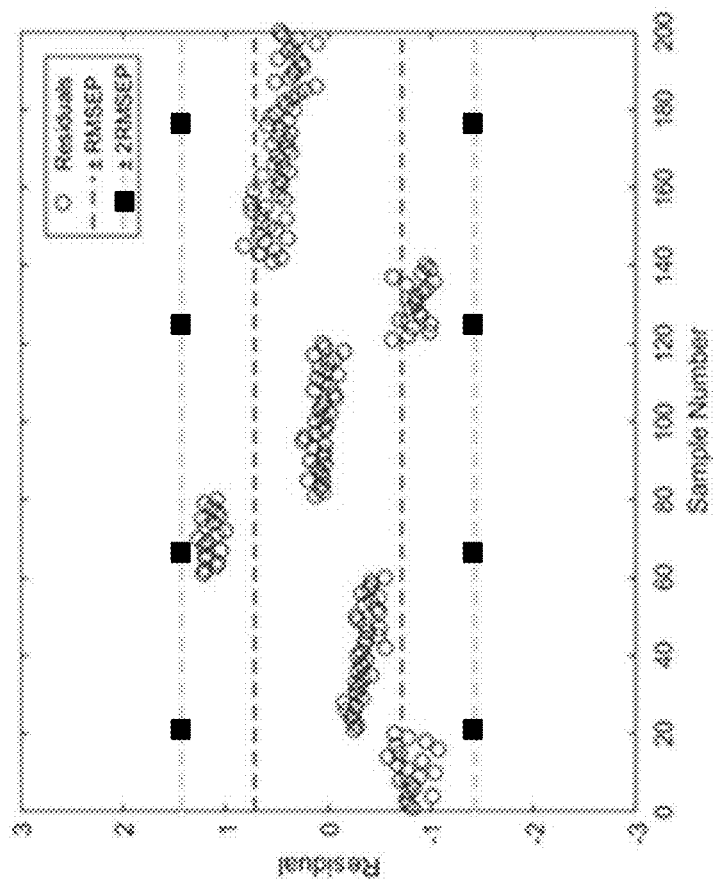
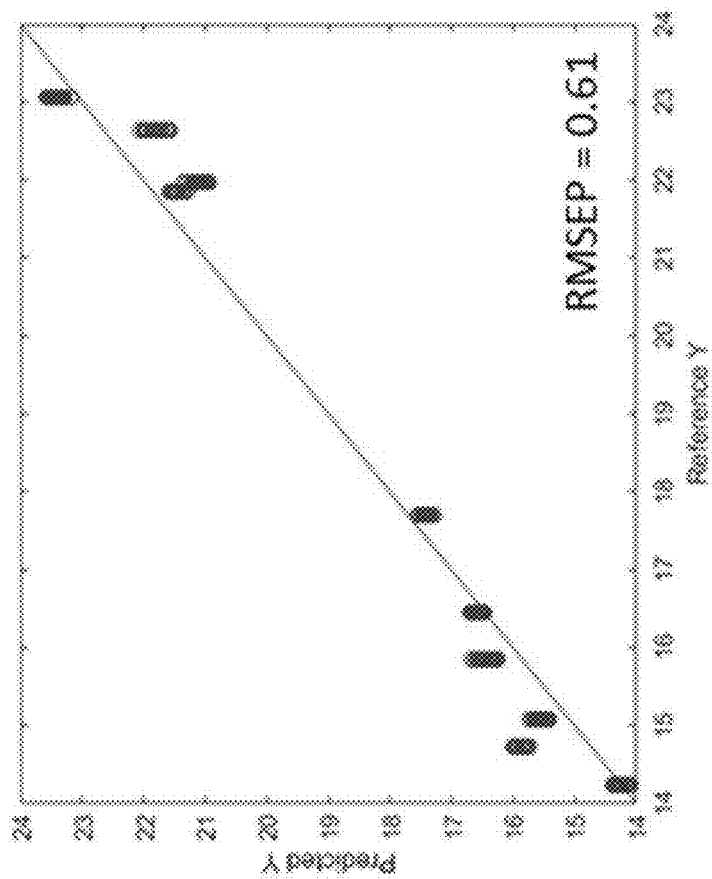
FIG. 10A
FIG. 10B

FOCUSING LINEAR MODEL CORRECTION AND LINEAR MODEL CORRECTION FOR MULTIVARIATE CALIBRATION MODEL MAINTENANCE

RELATED APPLICATION

This application is a continuation of U.S. patent application Ser. No. 16/032,978, filed Jul. 11, 2018, which is incorporated herein by reference in its entirety.

BACKGROUND

A spectroscopic instrument may be configured with a calibration model for calibrating spectroscopic measurements performed by the spectroscopic instrument. The calibration model is typically generated based on reference values, corresponding to known samples, and spectra, corresponding to the known samples, as measured by the spectroscopic instrument.

SUMMARY

According to some possible implementations, a method may include: obtaining, by a device, a master beta coefficient of a master calibration model associated with a master instrument, wherein the master beta coefficient is at a grid of a target instrument; performing, by the device, constrained optimization of an objective function, in accordance with a set of constraints, in order to determine a pair of transferred beta coefficients, wherein the constrained optimization is performed based on an initial pair of transferred beta coefficients, the master beta coefficient, and spectra associated with a scouting set; determining, by the device and based on the pair of transferred beta coefficients, a transferred beta coefficient; and determining, by the device, a final transferred beta coefficient based on a set of transferred beta coefficients including the transferred beta coefficient, wherein the final transferred beta coefficient is associated with generating a transferred calibration model, corresponding to the master calibration model, for use by the target instrument.

According to some possible implementations, a method may include: determining, by a device, that a grid of a master instrument, associated with master calibration model, does not match a grid of a target instrument for which a transferred calibration model, corresponding to the master calibration model, is to be generated; interpolating, by the device and based on determining that the grid of the master instrument does not match the grid of the target instrument, a beta coefficient of the master calibration model to the grid of the target instrument; and determining, by the device, a master beta coefficient, associated with generating the transferred calibration model, based on a result of interpolating the beta coefficient of the master calibration model to the grid of the target instrument.

According to some possible implementations, a method may include: obtaining, by a device, a scouting set associated with updating a calibration model, wherein the scouting set includes spectra associated with a set of samples based on which the calibration model is to be updated; determining, by the device, a beta coefficient associated with the calibration model; determining, by the device and based on the beta coefficient and using a linear model correction (LMC) technique, an updated beta coefficient associated with updating the calibration model; and updating, by the device, the calibration model based on the updated beta coefficient.

BRIEF DESCRIPTION OF THE DRAWINGS

FIGS. 1A-1C is a diagram of an overview of an example implementation described herein.

FIG. 6 is a flow chart of an example process for interpolating a beta coefficient of a master calibration model to a grid of a target instrument in order to determine a master beta coefficient for use with a focused linear model correction technique or a linear model correction technique, as described herein.

FIGS. 9A-9D, 10A, 10B, 11A, and 11B are diagrams illustrating example results associated with achieving standardization of a calibration model across multiple instruments are diagrams.

DETAILED DESCRIPTION

Figure 1C:
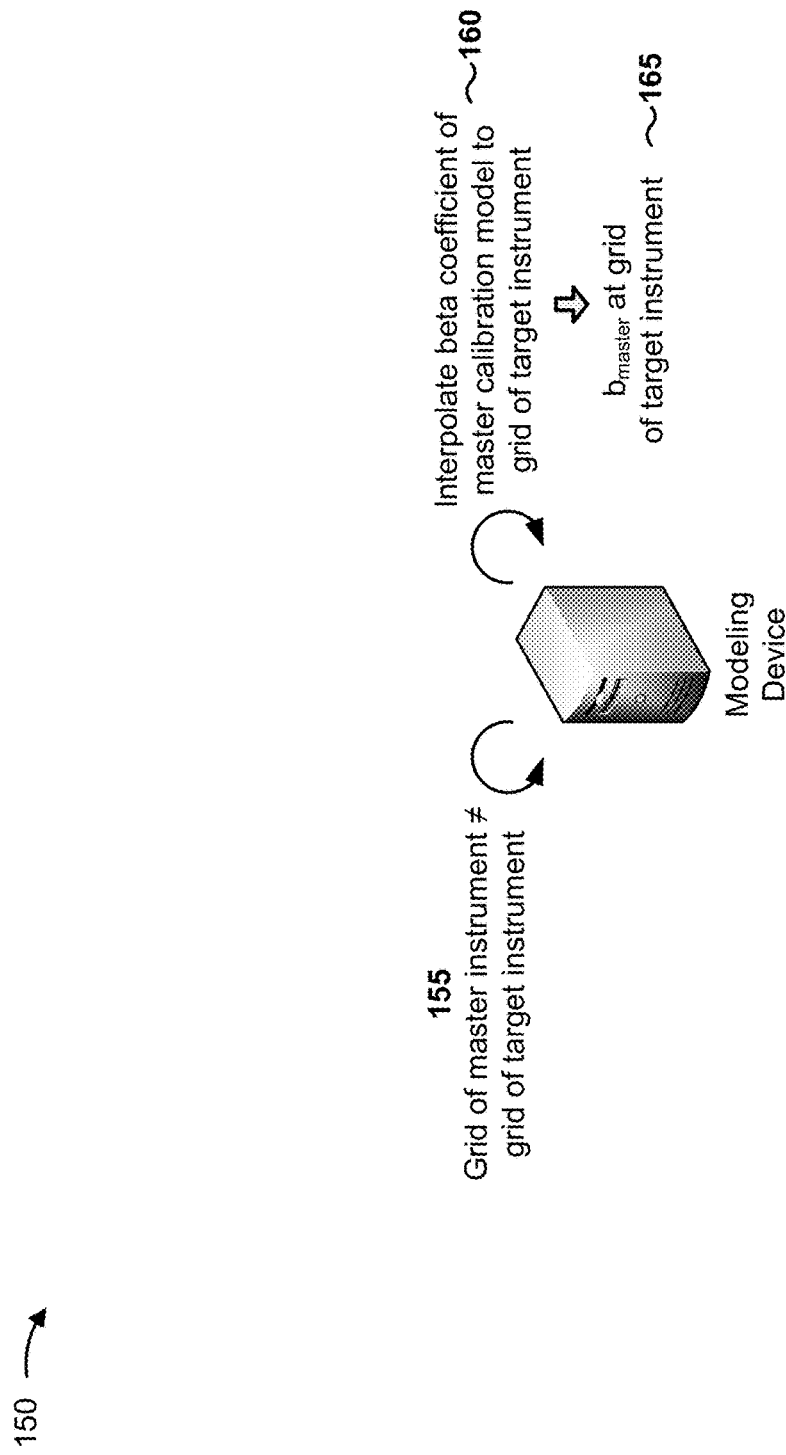

The following detailed description of example implementations refers to the accompanying drawings. The same reference numbers in different drawings may identify the same or similar elements.

Calibration model transfer and calibration model updating are two important areas in multivariate calibration model maintenance for spectroscopic applications, such as an application in the near-infrared (NIR) region.

In some cases, results are not acceptable when using a multivariate calibration model that is developed on a first spectroscopic instrument (or under one environmental condition) in order to predict a calibrated property for a sample measured on a second spectroscopic instrument (or under a different environmental condition by the first spectroscopic instrument). Further, even for the same spectroscopic instrument, a signal may drift over time, meaning that updating an existing calibration model would be required. When updating a calibration model, in order to avoid the cumbersome and expensive task of recollecting data and recalibrating the existing calibration model, calibration transfer techniques can be implemented in order to transfer a calibration model from one condition to another, regardless of sources of the drift.

One requirement of typical calibration model transfer techniques is acquisition of transfer data sets that include spectra from the same set of samples as collected by both a first instrument (e.g., a master instrument from which a calibration model is to be transferred, or a given instrument under an original condition) and a second instrument (e.g., a target instrument to which the calibration model is to be transferred, or the given instrument under a target condition). In some cases, obtaining the transfer data sets is difficult or impossible. For example, when a calibration model for a perishable material needs to be transferred from a master instrument that is located in one country to a target instrument located in another country, obtaining the transfer data sets may not be possible.

A linear model correction (LMC) technique may solve this issue by requiring only a few spectra collected only by the target instrument. The set of spectra used by the LMC technique is referred to as a scouting set. However, for the LMC technique to work, reference values (e.g., actual values as measured in, for example, a chemistry lab) for the scouting set are required. In some cases, obtaining these reference values can be quite time consuming and/or expensive.

Some implementations described herein provide a focused LMC (fLMC) technique that can be used in association with performing calibration model transfer. Similar to the LMC technique, the fLMC technique requires only a scouting set collected by the target instrument. However, unlike the LMC technique, the fLMC technique does not require reference values for the scouting set. As such, use of the fLMC technique in association with calibration model transfer reduces cost, difficulty, and/or complexity of calibration model transfer (e.g., as compared to the LMC technique, as well as typical calibration model transfer techniques described above).

Further, calibration model transfer from a master instrument with comparatively higher spectral resolution and/or a comparatively wider wavelength range to a target instrument with a comparatively lower spectral resolution and/or a comparatively narrower wavelength range is often encountered (e.g., when transferring a calibration model from a benchtop instrument to a portable instrument). For calibration model transfer in such a case, typical calibration transfer techniques require a full master calibration set (e.g., sets of spectra, associated with a set of samples, as measured by the master instrument) in order to initiate the calibration model transfer process. Here, spectra of the master calibration set are interpolated to a grid of the target instrument, and then an intermediate model is developed for transfer to the target instrument.

However, access to the master calibration set is not always possible. Even when the master calibration set is accessible, the master database may be large and/or may have a long history of maintenance, in some cases. As such, it may be difficult and/or time consuming to obtain a clean master calibration set from the database.

Some implementations described herein provide a procedure in which the fLMC technique or the LMC technique uses beta coefficients of a master calibration model in association with performing a calibration model transfer, without a need for the master calibration set. Use of the beta coefficients (rather than the master calibration set) reduces cost, difficulty, and/or complexity of the calibration model transfer.

Additionally, when a calibration model, developed on a master instrument is to be deployed on multiple other instruments that likely have instrument-to-instrument variations (e.g., multiple different target instruments), performing calibration model transfer using a conventional calibration model transfer technique may be difficult (e.g., when the target instruments are at locations far away from the master instrument). In some implementations, the LMC technique or the fLMC technique can be configured on the multiple target instruments in order to resolve this issue. When the master calibration model is delivered to the target instrument, a user need only to collect a scouting a set (e.g., spectra from a few samples associated with a given application). The calibration model can be automatically corrected using these spectra in conjunction with the LMC technique (e.g., when reference values are available) or the fLMC technique (e.g., regardless of whether the reference values are available).

Furthermore, as described above, calibration model updating may be needed after a calibration model is deployed on a given instrument (e.g., due to changes in samples, measurement environment, and/or the like). A typical technique for performing calibration model updating is to add new samples to the existing calibration set and then rebuild the calibration model. However, this technique may take a significant number of samples to make the calibration model fit for the new samples or new conditions. Further, this technique requires all the calibration data to be available. In addition, when the calibration database is large, particularly when the spectral range is wide and the spectral resolution is high, rebuilding the calibration model may consume a substantial amount of time and/or resources (e.g., processor resources, battery power, and/or the like). Thus, it may not be possible to update the calibration model during online operation of the instrument.

Some implementations described herein provide techniques for using the LMC technique for calibration model updating. Intrinsically, the LMC technique requires a relatively small number of samples in order to perform calibration model updating. In some implementations, an updating set (i.e., a scouting set associated with performing calibration model updating) can include samples representative of different conditions for future samples in order to make future prediction more accurate. Moreover, calibration model updating using the LMC technique is comparatively faster than the typical updating technique described above. For example, calibration model updating using the LMC procedure may be performed in seconds, thereby making calibration model updating during online operation possible.

In addition, in some cases, transfer sets from both a master instrument and a target instrument may be available, while reference values for the transfer sets may be unavailable. In such cases, as described here, the LMC technique can be performed using the transfer set from the target instrument as a scouting set, and using ref values predicted by the master calibration model for the transfer set from the master instrument as the reference values. Thus, the LMC technique can be performed when spectral data are available that could otherwise be used to perform other conventional calibration transfer techniques.

FIGS. 1A-1C are diagrams of example implementations described herein. FIGS. 1A and 1B are diagrams of an example implementation 100 associated with using a focused linear model correction (fLMC) correction technique in association with generating a transferred calibration model, for configuration on a target instrument, that corresponds to a master calibration model associated with a master instrument.

For the purposes of example implementation 100 of FIGS. 1A and 1B, a master calibration model, configured on a master instrument, is to be transferred to a target instrument. In other words, that a transferred calibration model, corresponding to the master calibration model configured on the master instrument, is to be generated for use by the target instrument. Example implementation 100 describes use a fLMC technique in association with generating the transferred calibration model.

As shown in FIG. 1A, and by reference number 105, a modeling device (e.g., a device associated with generating the transferred calibration model) may obtain a master beta coefficient of the master calibration model at a grid of the target instrument.

The master beta coefficient may include a set of coefficients associated with the master calibration model. For example, the master beta coefficient may include a vector of regression coefficients associated with a partial least squares (PLS) regression calibration model configured on the master instrument.

As noted above, the master beta coefficient is at the grid of the target instrument. The grid of the target instrument is a parameter of the target instrument defined by a spectral resolution and a wavelength range of the target instrument. Similarly, a grid of the master instrument is a parameter of the master instrument defined by a spectral resolution and a wavelength range of the master instrument. In some implementations, the grid of the master instrument may be different from the grid of the target instrument (e.g., when the master instrument has a comparatively higher spectral resolution and/or a wider wavelength range than those of the target instrument). Alternatively, the grid of the master instrument may match the grid of the target instrument (e.g., when the spectral resolution and the wavelength range of the master instrument match those of the target instrument within a threshold amount).

In some implementations, a manner in which the modeling device obtains the master beta coefficient may be based on whether the grid of the master instrument matches the grid of the target instrument.

For example, the modeling device may determine (e.g., based on information provided by the master instrument and/or the target instrument, based on information stored or accessible by modeling device) whether the grid of the master instrument matches the grid of the target instrument. In some implementations, if the modeling device determines that the grid of the master instrument matches the grid of the target instrument, then the modeling device may identify a beta coefficient of the master calibration model as the master beta coefficient. In other words, when the grid of the master instrument matches the grid of the target instrument, the modeling device may directly use the beta coefficient of the master instrument as the master beta coefficient (e.g., since the beta coefficient of the master calibration model is already at the grid of the target instrument). In such a case, the beta coefficient of the master calibration model can be used as the master beta coefficient irrespective of whether a master calibration set, associated with the master calibration model, is available.

In some implementations, if the modeling device determines that the grid of the master instrument does not match the grid of the target instrument, then the master instrument may obtain the master beta coefficient based on a master calibration set associated with the master calibration model.

For example, if the grid of the master instrument does not match the grid of the target instrument, then the modeling device may interpolate the master calibration set to the grid of the target instrument in order to create interpolated calibration data (i.e., spectra of the master calibration set interpolated to the grid of the target instrument). Here, the modeling device may generate a regression model (e.g., a PLS model, a principal component regression (PCR) model, and/or the like) based on the interpolated calibration data, and may determine the master beta coefficient as a beta coefficient of the regression model. In some implementations, the modeling device may obtain the master beta coefficient in this manner when the master calibration set is available. For example, the modeling device may determine that the master calibration set is available (e.g., accessible, not exceeding a threshold size or complexity level), and may proceed, as described above.

In some implementations, if the modeling device determines that the grid of the master instrument does not match the grid of the target instrument target instrument, then the master instrument may obtain the master beta coefficient based on a beta coefficient of the master calibration model, an example of which is illustrated in FIG. 1C.

FIG. 1C is a diagram of an example implementation 150 associated with interpolating a beta coefficient the master calibration model to a grid of the target instrument in order to obtain a master beta coefficient. As shown by reference number 155, the modeling device may determine that the grid of the master instrument does not match the grid of the target instrument. As shown by reference number 160, based on this determination, the modeling device may interpolate a beta coefficient of the master calibration model to the grid of the target instrument. As shown by reference number 165, a result of interpolating the beta coefficient of the master calibration model to the grid of the target instrument may be used as the master beta coefficient. In some implementations, the modeling device may obtain the master beta coefficient in this manner when the master calibration set is unavailable. For example, the modeling device may determine that the master calibration set is unavailable (e.g., not accessible, exceeding a threshold size or complexity level), and may proceed as described above.

In some implementations, the modeling device may determine the master beta coefficient based on interpolating the beta coefficient of the master calibration model to the grid of the target instrument in association with using the fLMC technique for a calibration model transfer (as described in association with example implementation 100). Additionally, or alternatively, a modeling device may determine the master beta coefficient based on interpolating the beta coefficient of the master calibration model to the grid of the target instrument in association with using the LMC technique. In other words, interpolation of the beta coefficient of the master calibration model to the grid of the target instrument may be used in association with performing the fLMC technique or the LMC technique for calibration model transfer.

Returning to the fLMC technique associated with example implementation 100, in some implementations, the modeling device may determine a final transferred beta coefficient based on a set of transferred beta coefficients. The final transferred beta coefficient is a beta coefficient to be used to generate the transferred calibration model. In some implementations, the modeling device may determine each of the set of transferred beta coefficients based on a respective iteration of a constrained optimization of an objective function, as described below.

In some implementations, for each iteration, the modeling device may perform constrained optimization of the following objective function:

$$\underset{b_{trans}}{\mathrm{argmin}}(\|X_{scout}b_{transA} - X_{scout}b_{transB}\|)^2$$

with the following constraints:

$$\mathrm{corr}(b_{transA}, b_{master}) \geq r \quad (1)$$

$$\mathrm{corr}(b_{transB}, b_{master}) \geq r \quad (2)$$

$$\mathrm{slope}(b_{transA}, b_{master}) \geq r \quad (3)$$

$$\mathrm{slope}(b_{transB}, b_{master}) \geq r \quad (4)$$

$$\mathrm{min}Y_{cal} << X_{scout}b_{transA} << \mathrm{max}Y_{cal} \quad (5)$$

$$\mathrm{min}Y_{cal} << X_{scout}b_{transB} << \mathrm{max}Y_{cal} \quad (6)$$

where $X_{scout}$ is the scouting set (e.g., spectra of the scouting set as measured by the target instrument), $b_{transA}$ and $b_{transB}$ are a pair of transferred beta coefficients associated with a given iteration, $b_{master}$ is the master beta coefficient, r is a constraint threshold, and $\mathrm{min}Y_{cal}$ and $\mathrm{max}Y_{cal}$ define a calibration range associated with the target instrument.

In some implementations, the constraint threshold r (e.g., the correlation constraint and/or the slope constraint, as described in the above equations above) may be optimized using a validation set. In such a case, a set of constraint threshold values r can be used iteratively and an optimal r (e.g., determined based on a root mean square error of prediction (RMSEP) of the validation set) can be used in association with determining a resulting transferred beta coefficient. In some implementations, this constraint threshold optimization may be used in association with the fLMC technique or the LMC technique.

A reproducibility concept is introduced in order to establish the objective function. Assuming that each of a pair of transferred beta coefficients, $b_{transA}$ and $b_{transB}$, can fit the scouting set, a difference in predicted values of the scouting set using $b_{transA}$ and $b_{transB}$ should be small. Therefore, the objective function is to minimize the squared difference in the predicted values of the scouting set using $b_{transA}$ and $b_{transB}$. By using this reproducibility concept, the need for reference values of the scouting set is removed. In other words, due to this reproducibility concept, the fLMC technique does not require reference values of the scouting set (unlike the LMC technique).

In order to obtain meaningful results, minimization of the objective function needs to be performed under a set of constraints. For example, the set of constraints may include a correlation constraint associated with the master beta coefficient ($b_{master}$) and each of the pair of transferred beta coefficients associated with a given iteration of the constrained optimization of the objective function ($b_{transA}$ and $b_{transB}$). According to this correlation constraint, correlation between $b_{transA}$ and $b_{master}$ and correlation between $b_{transB}$ and $b_{master}$ should satisfy a threshold (e.g., as indicated by equations (1) and (2), respectively, where the value r may be greater than or equal to 0.95, for example).

As another example, the set of constraints may include a slope constraint associated with the master beta coefficient and each of the pair of transferred beta coefficients associated with a given iteration of the constrained optimization of the object function. According to this slope constraint, a slope between $b_{transA}$ and $b_{master}$ and a slope between $b_{transB}$ and $b_{master}$ should satisfy a threshold (e.g., as indicated by equations (3) and (4), respectively, where the value r may be greater than or equal to 0.95, for example).

As another example, the set of constraints may include a calibration range constraint for predicted values associated with the scouting set. According to this calibration constraint, the value of the scouting set as predicted using $b_{transA}$ (i.e., $X_{scout}b_{transA}$) and the value of the scouting set as predicted by $b_{transB}$ (i.e., $X_{scout}b_{transB}$) should be within a calibration range (e.g., as indicated by equations (5) and (6), respectively) or in range close to reference values of the scouting set.

In order to start a given iteration of the above constrained optimization procedure, initial values of $b_{transA}$ and $b_{transB}$ are needed (i.e., $b_{transA0}$ and $b_{transB0}$, respectively). In some implementations, the modeling device may generate the initial pair of transferred beta coefficients based on random generation of the initial pair of transferred beta coefficients. Additionally, or alternatively, the modeling device may generate the initial pair of transferred beta coefficients based on applying a linear function, associated with a random value, to the master beta coefficient (e.g., $b_{transA0}$, $b_{transB0}$=m×$b_{master}$+n, where m and n are random numbers). Additionally, or alternatively, the modeling device may generate the initial pair of transferred beta coefficients based on adding a random value to the master beta coefficient (e.g., $b_{transA0}$, $b_{transB0}$=$b_{master}$ n, where n is a random number).

For a given iteration of constrained optimization, the modeling device may generate a pair of initial transferred beta coefficients (e.g., $b_{transAi0}$ and $b_{transBi0}$ for iteration i, and $b_{transAk0}$ and $b_{transBk0}$ for iteration k), and may perform constrained optimization of the object function in order to determine a pair of transferred beta coefficients (e.g., $b_{transAi}$ and $b_{transBi}$ for iteration i, and $b_{transAk}$ and $b_{transBk}$ for iteration k). Then, the modeling device may then determine a transferred beta coefficient based on the pair of transferred beta coefficients (e.g., $b_{transi}$ for iteration i, and $b_{transk}$ for iteration k). For example, as shown by reference number 110 with respect to iteration i, the modeling device may generate $b_{transAi0}$ and $b_{transBi0}$, perform constrained optimization of the object function in order to determine $b_{transAi}$ and $b_{transBi}$, and determine a transferred beta coefficient associated with iteration i ($b_{transi}$) based on the pair of transferred beta coefficients (e.g., based on averaging $b_{transAi}$ and $b_{transBi}$). As another example, as shown by reference number 115 with respect to iteration k, the modeling device may generate $b_{transAk0}$ and $b_{transBk0}$, perform constrained optimization of the object function in order to determine $b_{transAk}$ and b and transBk, determine a transferred beta coefficient associated with iteration k ($b_{transk}$) based on the pair of transferred beta coefficients (e.g., based on averaging $b_{transAk}$ and $b_{transBk}$). Here, $b_{transi}$ and $b_{transk}$ are included in the set of transferred beta coefficients based on which the modeling device may determine the final transferred beta coefficient ($b_{trans}$).

In some implementations, the modeling device may be configured to perform multiple (e.g., 5, 20, 100, and/or the like) iterations of constrained optimization of the objective function (e.g., in order to avoid bias results based on the randomized nature of the initial pair of transferred beta coefficients).

As shown in FIG. 1B, and by reference number 120, the modeling device may determine the final transferred beta coefficient ($b_{trans}$) based on the set of transferred beta coefficients. For example, the modeling device may determine the final transferred beta coefficient as being equal to a mean, a median, a mode, and/or the like, of the set of transferred beta coefficients (e.g., $b_{transi}$ through $b_{transk}$).

As shown by reference number 125, the modeling device may generate the transferred calibration model based on the final transferred beta coefficient. For example, the modeling device may generate a regression model (e.g., a PLS model, a PCR model, and/or the like) based on the final transferred beta coefficient. As shown by reference number 130, the modeling device may provide the transferred calibration model to the target instrument (e.g., such that the target instrument can use the transferred calibration model). In this way, the modeling device may be configured to use a fLMC technique that allows the modeling device to generate a transferred calibration model using spectra associated with a scouting set, without a need for reference values of the scouting set.

As indicated above, FIGS. 1A-1C are provided merely as examples. Other examples are possible and may differ from what was described with regard to FIGS. 1A-1C.

Figure 2:
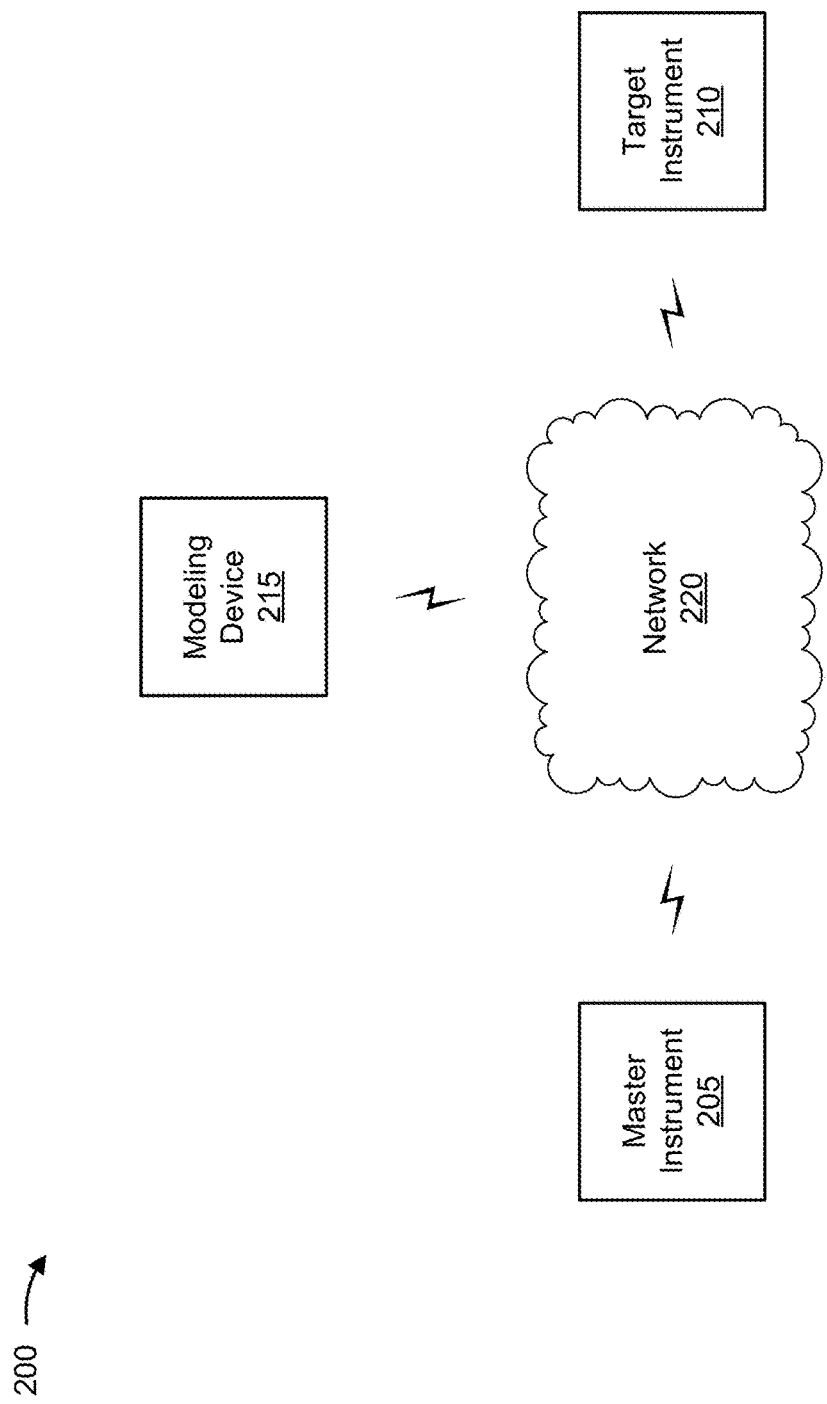
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a master instrument 205, a target instrument 210, a modeling device 215, and a network 220. Devices of environment 200 may interconnect via wired connections, wireless connections, or a combination of wired and wireless connections.

Master instrument 205 includes a device, configured with a master calibration model, that is capable of performing a spectroscopic measurement on a sample. For example, master instrument 205 may include a desktop (i.e., non-handheld) spectrometer device that performs spectroscopy (e.g., vibrational spectroscopy, such as near infrared (NIR) spectroscopy, mid-infrared spectroscopy (mid-IR), Raman spectroscopy, or the like). In some implementations, master instrument 205 may be capable of obtaining spectroscopic measurements at a higher resolution than spectroscopic measurements obtained by target instrument 210 (i.e., master instrument 205 may be a high-resolution device, while target instrument 210 may be a low-resolution device). For example, master instrument 205 may be capable of obtaining spectroscopic measurements on 400 channels, while target instrument 210 may be capable of obtaining spectroscopic measurement on 125 channels. In some implementations, master instrument 205 may be configured with a master calibration model for calibrating spectroscopic measurements obtained by master instrument 205. In some implementations, master instrument 205 may receive information from and/or transmit information to another device in environment 200, such as modeling device 215.

Target instrument 210 includes a device capable of performing a spectroscopic measurement on a sample based on a target calibration model, where the target calibration model may be generated based on information associated with a master calibration model associated with master instrument 205, as described herein. For example, target instrument 210 may include a mobile spectrometer device or a handheld spectrometer device that performs spectroscopy. In some implementations, target instrument 210 may be capable of obtaining spectroscopic measurements at a lower resolution than spectroscopic measurements obtained by master instrument 205. In some implementations, target instrument 210 may receive information from and/or transmit information to another device in environment 200, such as modeling device 215.

Modeling device 215 includes a device capable of performing operations associated with transferring a master calibration model from master instrument 205 to target instrument 210 (i.e., generating a transferred calibration model corresponding to the master calibration model) and/or updating a calibration model configured on a given instrument (e.g., master instrument 205 or target instrument 210) as described herein. For example, modeling device 215 may include a server, a group of servers, a computer, a cloud computing device, or the like. In some implementations, modeling device 215 may receive information from and/or transmit information to another device in environment 200, such as master instrument 205 and/or target instrument 210. In some implementations, modeling device 215 and master instrument 205 may be implemented within a single device. Alternatively, modeling device 215 and target instrument 210 may be implemented within a single device, in some implementations.

Network 220 includes one or more wired and/or wireless networks. For example, network 220 may include a cellular network (e.g., a New Radio (NR/5G) network, a long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2.

Furthermore, two or more devices shown in FIG. 2 may be implemented within a single device, or a single device shown in FIG. 2 may be implemented as multiple, distributed devices. For example, although master instrument 205 and modeling device 215 are described as being two separate devices, master instrument 205 and modeling device 215 may be implemented within a single device. As another example, target instrument 210 and modeling device 215 may be implemented within a single device. Additionally, or alternatively, a set of devices (e.g., one or more devices) of environment 200 may perform one or more functions described as being performed by another set of devices of environment 200.

Figure 3:
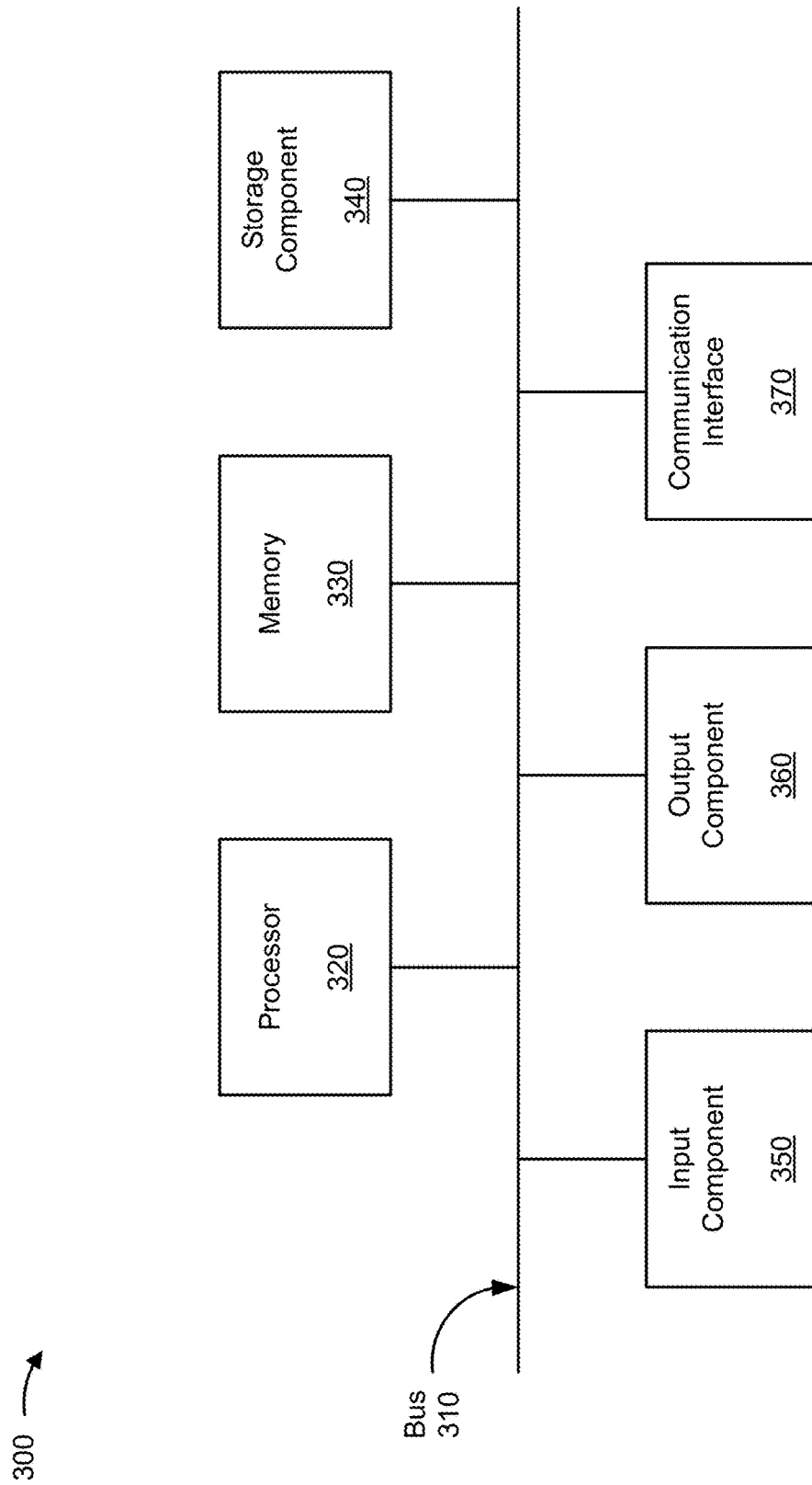
FIG. 3 is a diagram of example components of one or more devices of FIG. 2.

FIG. 3 is a diagram of example components of a device 300. Device 300 may correspond to master instrument 205, target instrument 210, and/or modeling device 215. In some implementations, master instrument 205, target instrument 210, and/or modeling device 215 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 takes the form of a central processing unit (CPU), a graphics processing unit (GPU), an accelerated processing unit (APU), a microprocessor, a microcontroller, a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
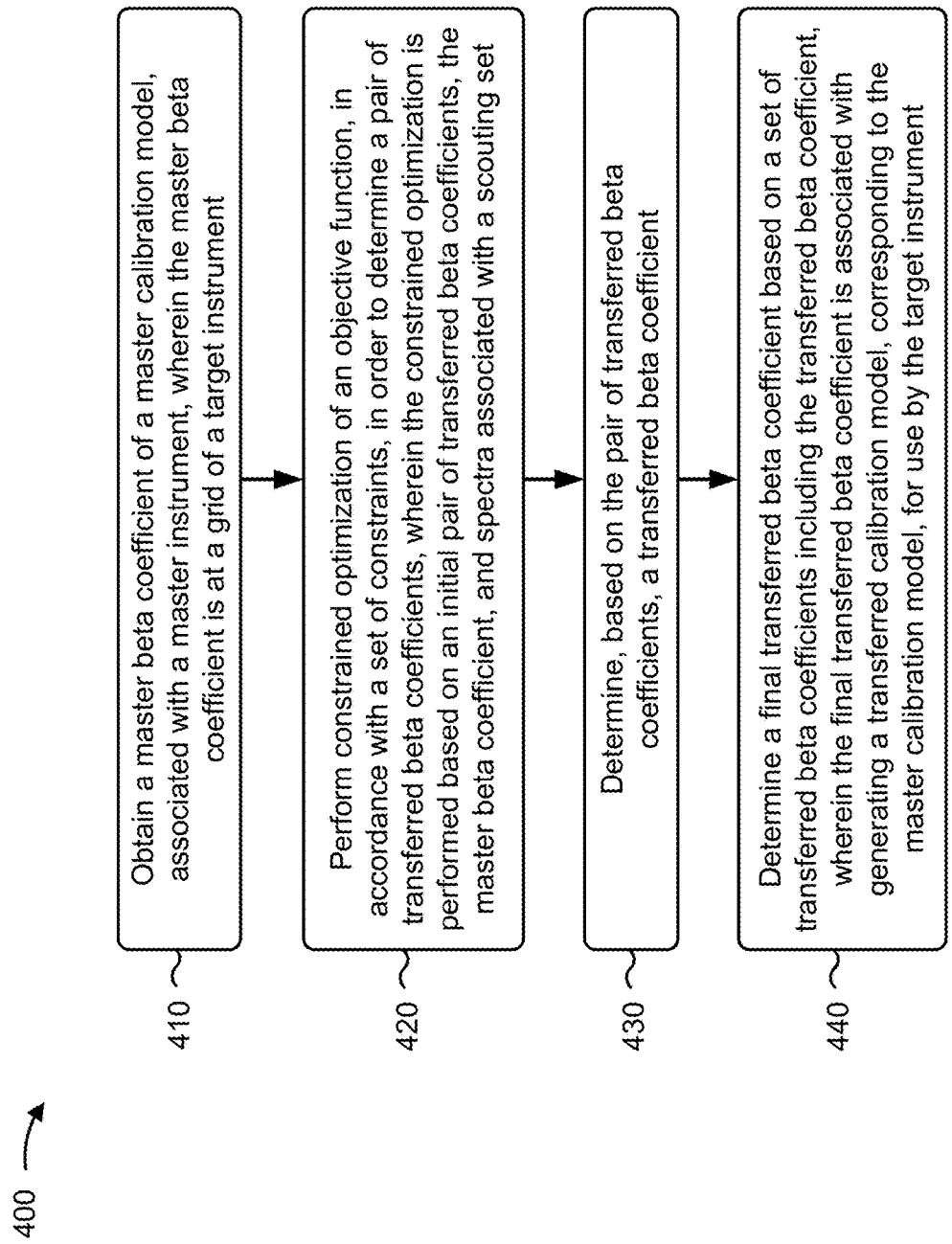
FIG. 4 is a flow chart of an example process of a focused linear model correction technique associated with determining a transferred beta coefficient for generating a transferred calibration model, as described herein.

FIG. 4 is a flow chart of an example process 400 of a focused linear model correction (fLMC) technique associated with determining a transferred beta coefficient for generating a transferred calibration model, as described herein. In some implementations, one or more process blocks of FIG. 4 may be performed by modeling device 215. In some implementations, one or more process blocks of FIG. 4 may be performed by another device or a group of devices separate from or including modeling device 215, such as master instrument 205 and/or target instrument 210.

As shown in FIG. 4, process 400 may include obtaining a master beta coefficient of a master calibration model associated with a master instrument, wherein the master beta coefficient is at a grid of a target instrument (block 410). For example, modeling device 215 may obtain a master beta coefficient of a master calibration model associated with master instrument 205, wherein the master beta coefficient is at a grid of target instrument 210, as described above.

As further shown in FIG. 4, process 400 may include performing constrained optimization of an objective function, in accordance with a set of constraints, in order to determine a pair of transferred beta coefficients, wherein the constrained optimization is performed based on an initial pair of transferred beta coefficients, the master beta coefficient, and spectra associated with a scouting set (block 420). For example, modeling device 215 may perform constrained optimization of an objective function, in accordance with a set of constraints, in order to determine a pair of transferred beta coefficients, wherein the constrained optimization is performed based on an initial pair of transferred beta coefficients, the master beta coefficient, and spectra associated with a scouting set, as described above.

As further shown in FIG. 4, process 400 may include determining, based on the pair of transferred beta coefficients, a transferred beta coefficient (block 430). For example, modeling device 215 may determine, based on the pair of transferred beta coefficients, a transferred beta coefficient, as described above.

As further shown in FIG. 4, process 400 may include determining a final transferred beta coefficient based on a set of transferred beta coefficients including the transferred beta coefficient, wherein the final transferred beta coefficient is associated with generating a transferred calibration model, corresponding to the master calibration model, for use by the target instrument (block 440). For example, modeling device 215 may determine a final transferred beta coefficient based on a set of transferred beta coefficients including the transferred beta coefficient, wherein the final transferred beta coefficient is associated with generating a transferred calibration model, corresponding to the master calibration model, for use by target instrument 210.

Process 400 may include additional implementations, such as any single implementation or any combination of implementations described below and/or in connection with one or more other processes described elsewhere herein.

In some implementations, modeling device 215 and/or target instrument 210 may generate the transferred calibration model based on the final transferred beta coefficient.

In some implementations, the set of transferred beta coefficients includes at least one other transferred beta coefficient, each being determined based on a respective performance of constrained optimization of the objective function based on respective initial pairs of transferred beta coefficients.

In some implementations, when obtaining the master beta coefficient, modeling device 215 may determine that a grid of master instrument 205 matches the grid of target instrument 210, and identify the beta coefficient of the master calibration model as the master beta coefficient.

In some implementations, when obtaining the master beta coefficient, modeling device 215 may determine that a grid of master instrument 205 does not match the grid of target instrument 210; interpolate, based on determining that the grid of master instrument 205 does not match the grid of target instrument 210, a master calibration set to the grid of target instrument 210 in order to create interpolated calibration data; generate a regression model based on the interpolated calibration data; and determine the master beta coefficient as a beta coefficient of the regression model.

In some implementations, when obtaining the master beta coefficient, modeling device 215 may determine that a grid of master instrument 205 does not match the grid of target instrument 210; interpolate a beta coefficient of the master calibration model to the grid of target instrument 210 based on determining that the grid of master instrument 205 does not match the grid of target instrument 210; and determine the master beta coefficient based on a result of interpolating the beta coefficient of the master calibration model to the grid of target instrument 210. In some implementations, the beta coefficient of the master calibration model is interpolated to the grid of target instrument 210 based on a determination that a master calibration set, associated with the master calibration model, is unavailable.

In some implementations, the set of constraints includes a correlation constraint associated with the master beta coefficient and each of the pair of transferred beta coefficients, and/or a slope constraint associated with the master beta coefficient and each of the pair of transferred beta coefficients, in addition to a calibration range constraint for predicted values associated with the scouting set.

In some implementations, modeling device 215 may generate the initial pair of transferred beta coefficients based on random generation of the initial pair of transferred beta coefficients, applying a linear function, associated with a random value, to the master beta coefficient, and/or adding a random value to the master beta coefficient.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5A:
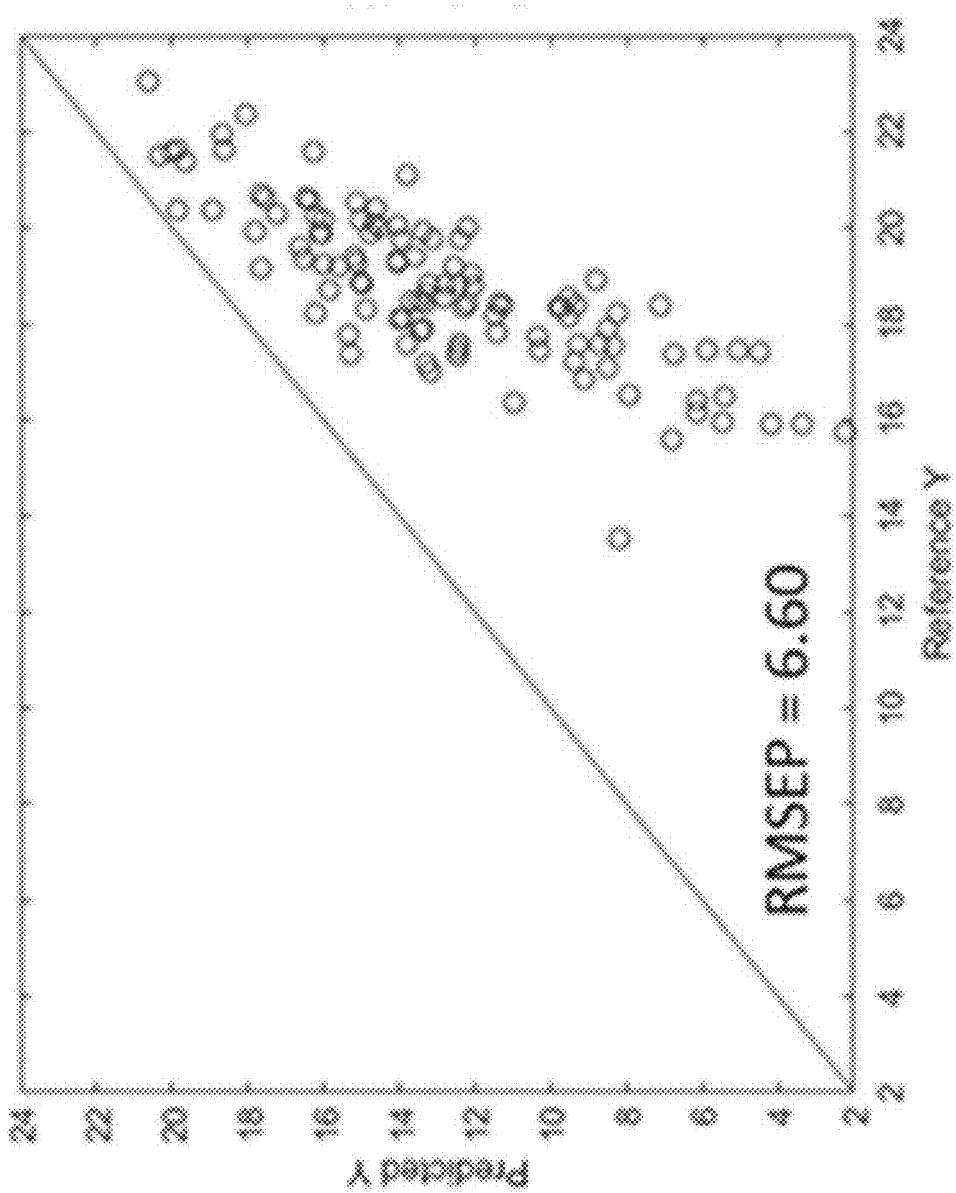
FIGS. 5A-5C are example diagrams associated with the focused linear model correction technique of FIG. 4.
Figure 5B:
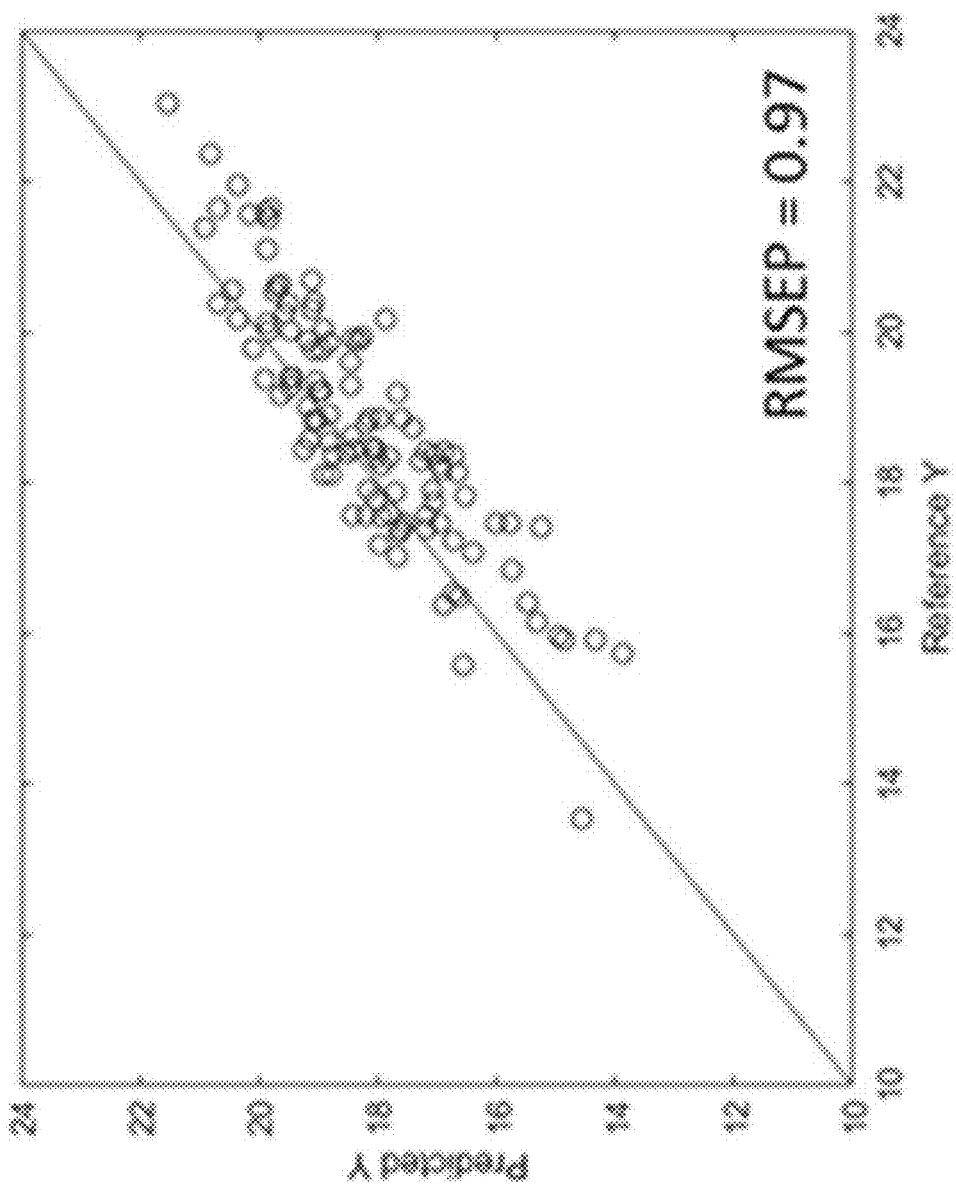
Figure 5C:
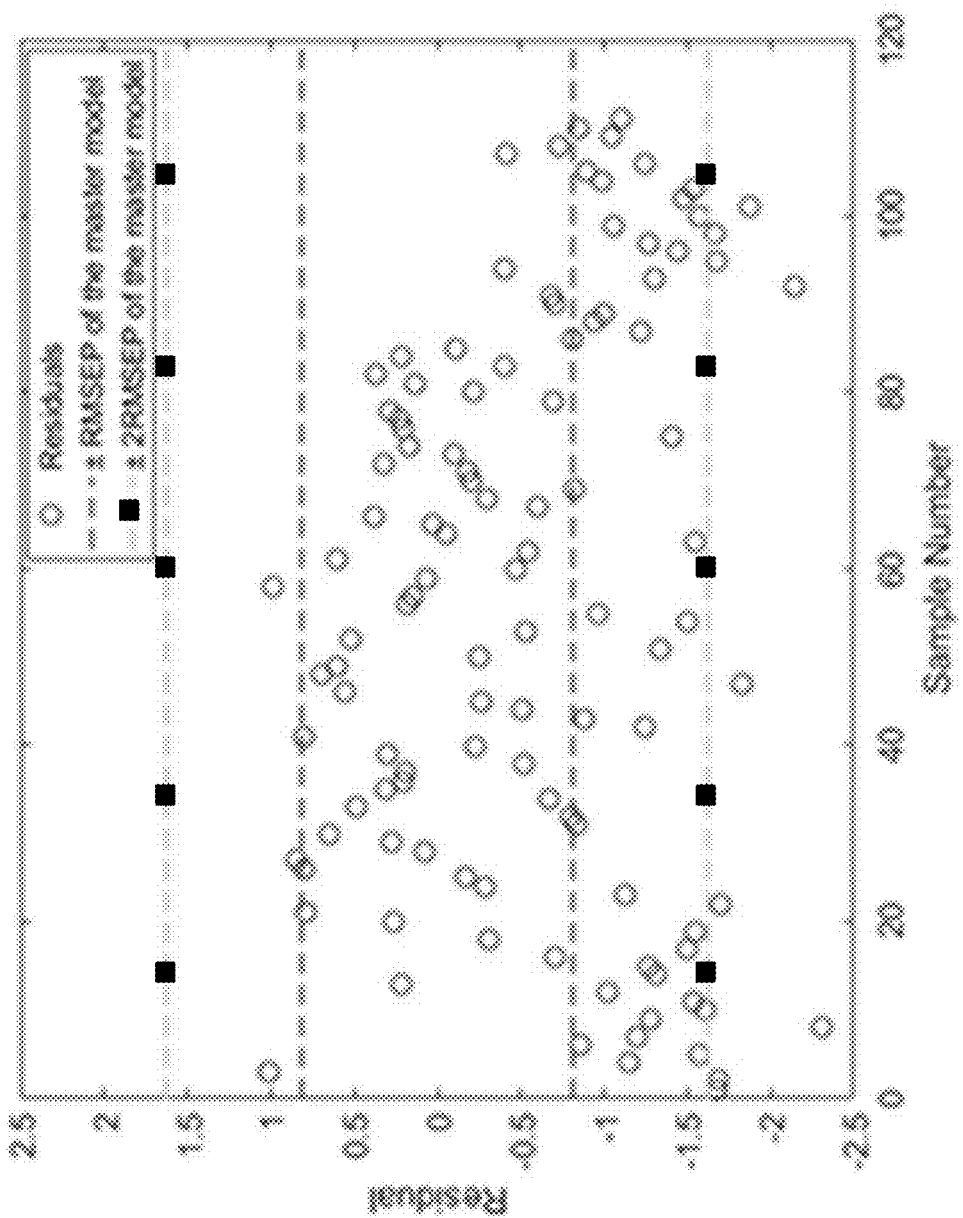

In order to illustrate the effectiveness of the fLMC technique, a PLS regression model for Brix of sugarcane was transferred from a benchtop FOSS NIR master instrument to a portable MicroNIR target instrument. FIGS. 5A-5C are diagrams associated with a result of this example calibration model transfer using the fLMC technique.

In total, 1712 FOSS spectra were used to build the master calibration model. These spectra were first interpolated to the MicroNIR grid. An intermediate master calibration model was built using these interpolated calibration data and the resulted beta coefficients were used as $b_{master}$. There were 126 spectra collected by the MicroNIR instrument, out of which 15 spectra were randomly selected as the scouting set to perform fLMC. The rest of the 111 spectra were used as an external validation set to validate the transferred calibration model. Prediction performance of the transferred calibration model was compared with that of the master calibration model using FOSS validation set from the same 111 samples.

As shown in FIG. 5A, without performing calibration model transfer, a root mean square error for prediction (RMSEP) was high when using the intermediate master calibration model to predict the MicroNIR validation set. However, when calibration model transfer was performed using the fLMC technique, RMSEP was significantly reduced, as shown in FIG. 5B. The RMSEP using the original FOSS model for the FOSS validation set was also calculated and used as a benchmark to evaluate performance of the transferred calibration model. In FIG. 5C, it can be seen that residuals between the predicted Brix values and the lab Brix values for the validation set by the transferred calibration model stayed within approximately ±2RMSEP of the original FOSS master calibration model, indicating approximately 95% confidence that the transferred MicroNIR calibration lies within the original bounds of the FOSS calibration. These results indicate that performance of the transferred calibration model, generated using the fLMC technique, is close to the original FOSS master calibration model (e.g., that has a comparatively wider wavelength range and a comparatively higher spectral resolution).

In addition, for comparison, the same FOSS master calibration model was transferred to MicroNIR using a mean difference correction (MDC) technique and piecewise direct standardization (PDS) technique, which are two typical techniques for calibration model transfer. In order to apply these two techniques, transfer sets consisting of 15 spectra from both the master instrument and the target instrument were used. These spectra were from the same samples as used in the scouting set when using the fLMC technique. RMSEP for the same validation set was 1.80 and 0.72 using the transferred calibration models by MDC and PDS, respectively. Thus, the fLMC technique performed better than the MDC technique and worse than the PDS technique in this case. However, unlike the PDS technique, the fLMC technique does not require the transfer set on the master instrument, thereby making the fLMC technique comparatively less costly and/or complex, while achieving similar performance.

As indicated above, FIGS. 5A-5C are provided merely as examples. Other examples are possible and may differ from what was described with regard to FIGS. 5A-5C.

FIG. 6 is a flow chart of an example process 600 for interpolating a beta coefficient of a master calibration model to a grid of a target instrument in order to determine a master beta coefficient for use with a fLMC technique or a LMC technique. In some implementations, one or more process blocks of FIG. 6 may be performed by modeling device 215. In some implementations, one or more process blocks of FIG. 6 may be performed by another device or a group of devices separate from or including modeling device 215, such as master instrument 205 and/or target instrument 210.

As shown in FIG. 6, process 600 may include determining that a grid of a master instrument, associated with master calibration model, does not match a grid of a target instrument for which a transferred calibration model, corresponding to the master calibration model, is to be generated (block 610). For example, modeling device 215 may determine that a grid of master instrument 205, associated with master calibration model, does not match a grid of target instrument 210 for which a transferred calibration model, corresponding to the master calibration model, is to be generated, as described above.

As further shown in FIG. 6, process 600 may include interpolating, based on determining that the grid of the master instrument does not match the grid of the target instrument, a beta coefficient of the master calibration model to the grid of the target instrument (block 620). For example, modeling device 215 may interpolate, based on determining that the grid of master instrument 205 does not match the grid of target instrument 210, a beta coefficient of the master calibration model to the grid of target instrument 210, as described above.

As further shown in FIG. 6, process 600 may include determining a master beta coefficient, associated with generating the transferred calibration model, based on a result of interpolating the beta coefficient of the master calibration model to the grid of the target instrument (block 630). For example, modeling device 215 may determine a master beta coefficient, associated with generating the transferred calibration model, based on a result of interpolating the beta coefficient of the master calibration model to the grid of target instrument 210, as described above.

Process 600 may include additional implementations, such as any single implementation or any combination of implementations described below and/or in connection with one or more other processes described elsewhere herein.

In some implementations, the beta coefficient of the master calibration model is interpolated to the grid of target instrument 210 based on a determination that a master calibration set, associated with the master calibration model, is unavailable.

In some implementations, modeling device 215 may perform constrained optimization of an objective function, in accordance with a set of constraints, in order to determine a pair of transferred beta coefficients, wherein the constrained optimization is performed based on an initial pair of transferred beta coefficients, the master beta coefficient, and spectra associated with a scouting set. Here, modeling device may determine, based on the pair of transferred beta coefficients, a transferred beta coefficient; may determine a final transferred beta coefficient based on a set of transferred beta coefficients including the transferred beta coefficient. In other words, in some implementations, modeling device 215 may determine the final transferred beta coefficient using a fLMC technique. In some implementations, the set of constraints includes a correlation constraint associated with the master beta coefficient and each of the pair of transferred beta coefficients, a slope constraint associated with the master beta coefficient and each of the pair of transferred beta coefficients, and a calibration range constraint for predicted values associated with the scouting set. In some implementations, modeling device 215 may generate the initial pair of transferred beta coefficients based on random generation of the initial pair of transferred beta coefficients, applying a linear function, associated with a random value, to the master beta coefficient, or adding a random value to the master beta coefficient In some implementations, modeling device 215 may determine, based on the master beta coefficient and using a linear model correction (LMC) technique, a transferred beta coefficient associated with generating the transferred calibration model. In other words, in some implementations, modeling device 215 may determine the final transferred beta coefficient using a LMC technique. In some implementations, reference values for a scouting set, associated with using the LMC technique, are predicted based on the master calibration model and a master transfer set.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

In some implementations, a beta coefficient of a master calibration model can be interpolated to a grid of target instrument 210 and used as the master beta coefficient, as described above. For example, in some implementations, this technique can be used in conjunction with the LMC technique or the fLMC technique. FIGS. 7A-7C and FIGS. 8A and 8B are diagrams associated with interpolating a beta coefficient of a master calibration model to a grid of a target instrument, and using the LMC technique and the fLMC technique, respectively, in association with performing calibration model transfer.

Figure 7A:
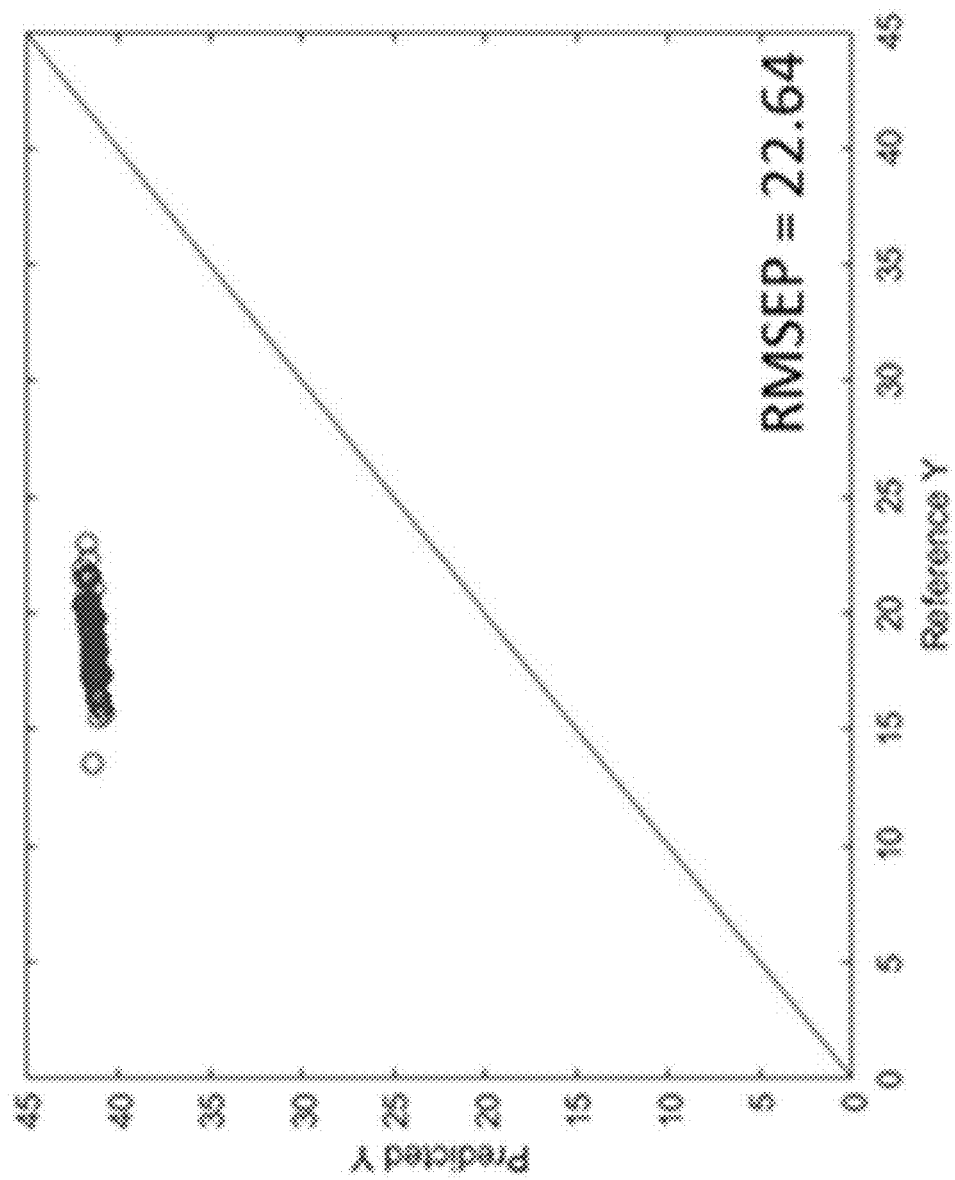
FIGS. 7A-7C and 8A and 8B are diagrams associated with interpolating a beta coefficient of a master calibration model to a grid of a target instrument, and using the LMC technique and the fLMC technique, respectively, in association with performing calibration model transfer.
Figure 7B:
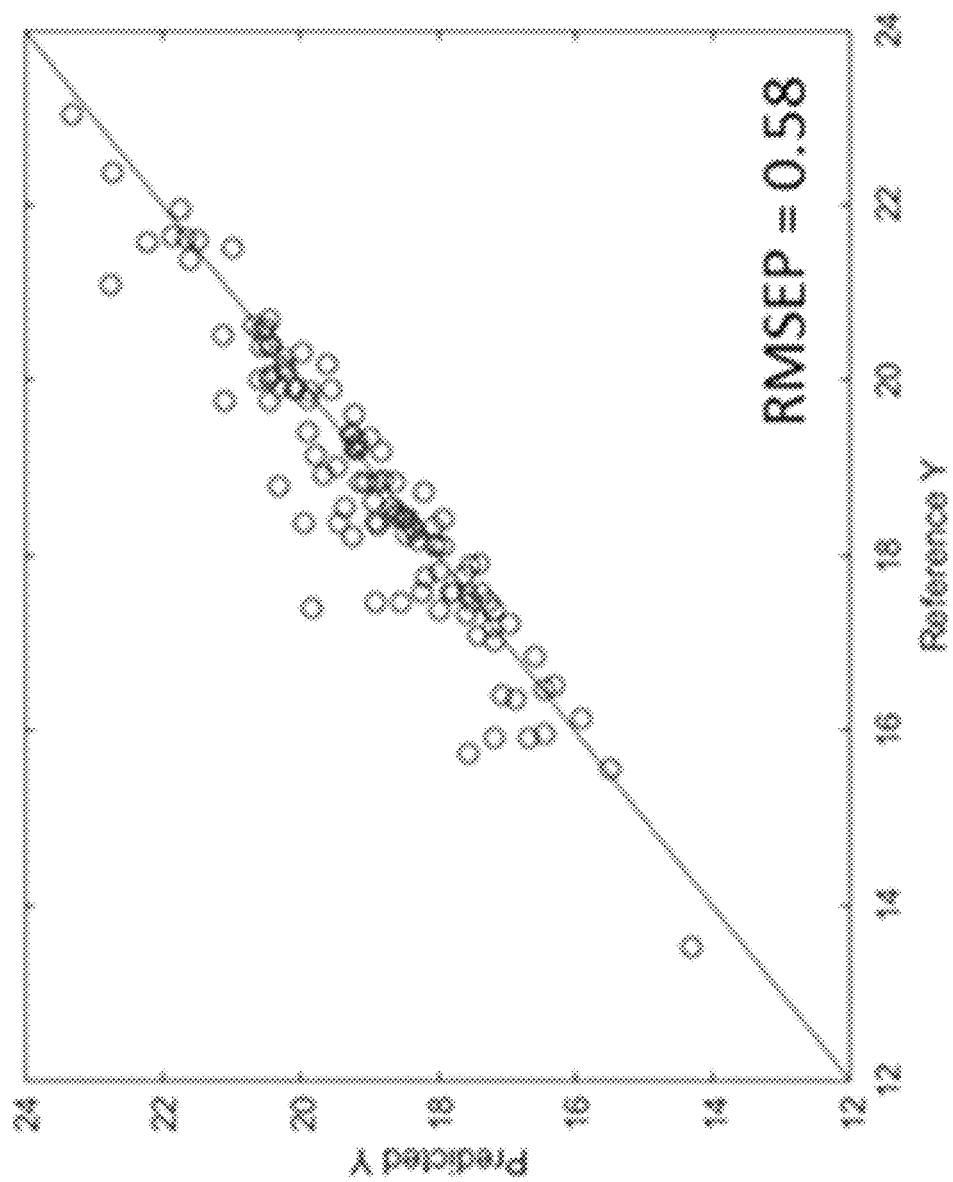
Figure 7C:
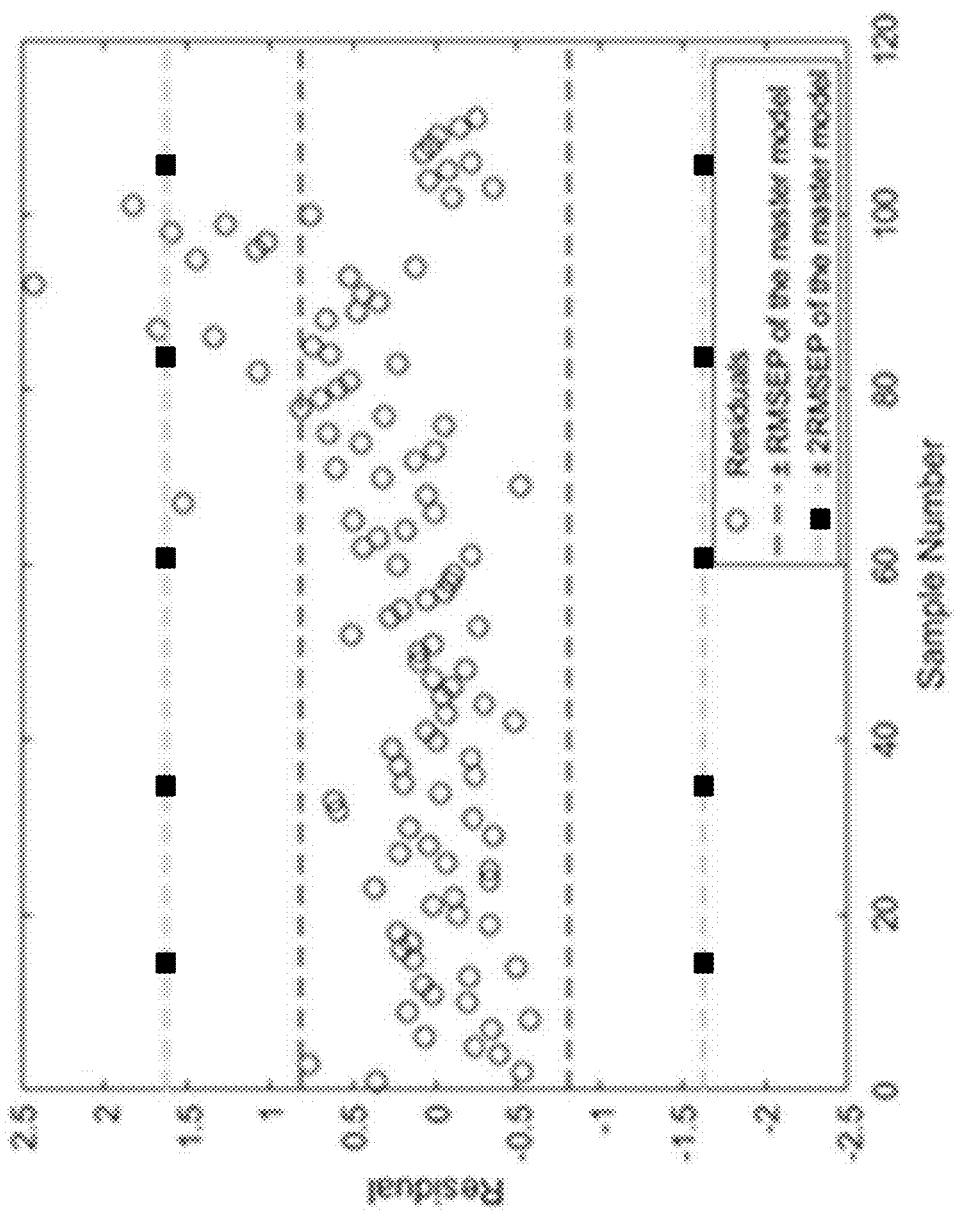

Using the same data sets as described above with regard to FIGS. 5A-5C, the LMC technique was performed using a result of interpolating a beta coefficient of a master calibration model to a grid of target instrument as a master beta coefficient, the results of which are shown in FIGS. 7A-7C. Here, since there is no master calibration set available, it is not possible to build an intermediate master calibration model. As shown in FIG. 7A, when directly using the interpolated beta coefficients to predict the validation set on the target instrument, the resulted RMSEP was high. As shown in FIG. 7B, when using the interpolated beta coefficients as the master beta coefficient and performing the LMC technique, the RMSEP was significantly reduced. Further, as shown in FIG. 7C, residuals between the predicted Brix values and the lab Brix values for the validation set by the transferred calibration model stayed within ±2RMSEP of the original FOSS master calibration model, with limited exceptions.

Figure 8A:
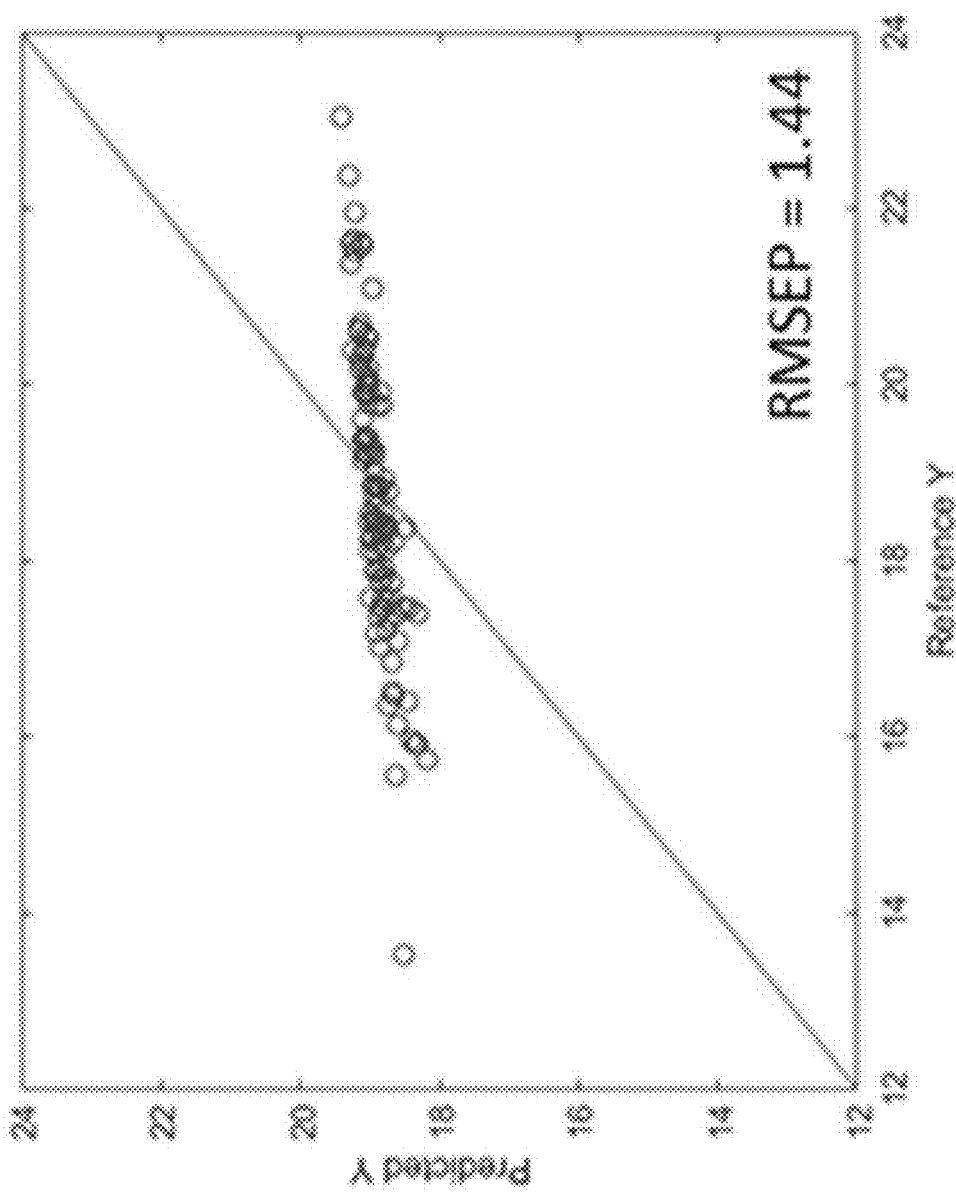
Figure 8B:
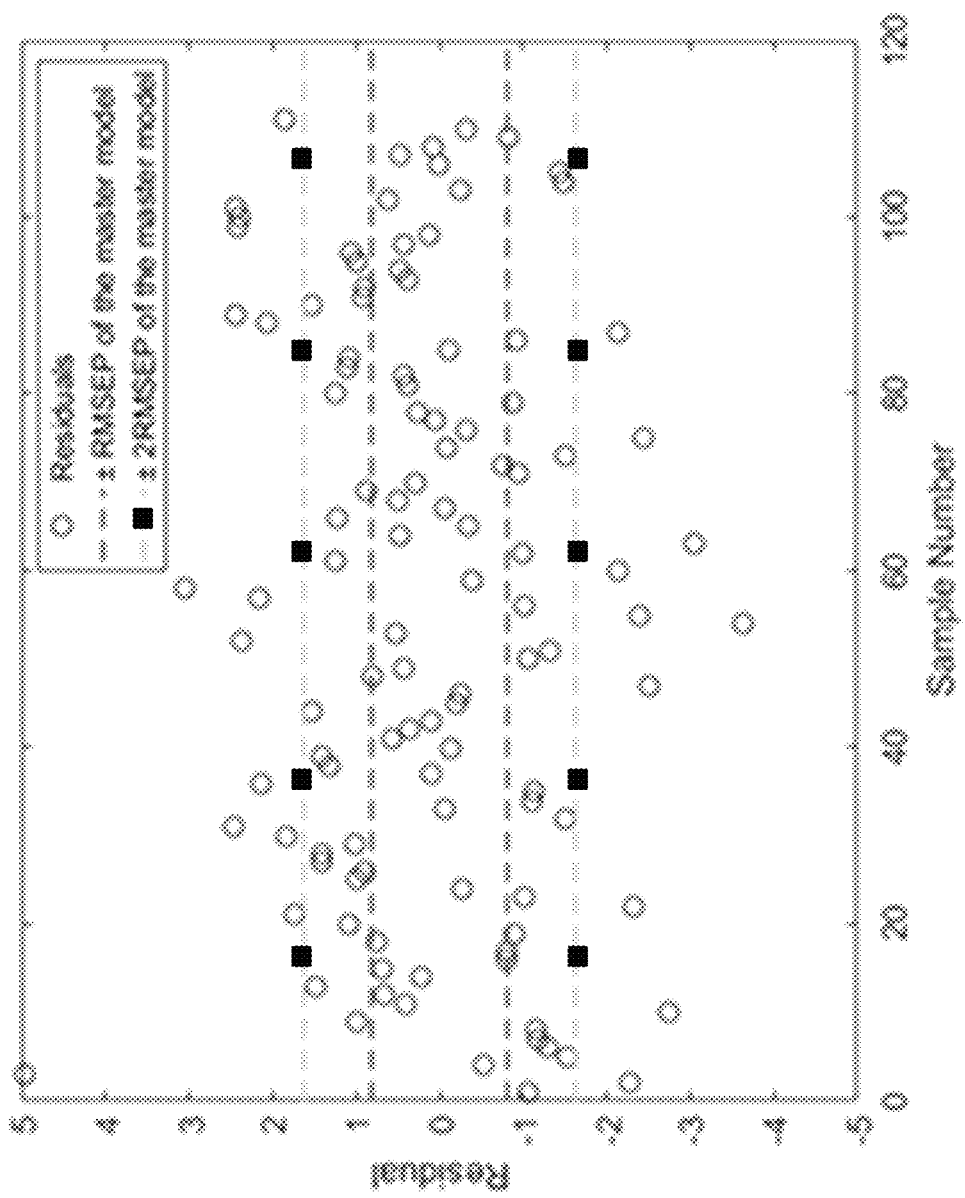

Further, using the same data sets as described above with regard to FIGS. 5A-5C, the fLMC technique was performed using a result of interpolating the beta coefficient of the master calibration model to the grid of the target instrument as the master beta coefficient, the results are shown in FIGS. 8A and 8B. Although performance was slightly reduced as compared to using the LMC technique, the RMSEP was significantly reduced compared to that without performing calibration model transfer (as shown in FIG. 5A). As shown in FIG. 8A, the RMSEP was reasonably low with a normalized RMSEP of 7.7% (normalized to the mean Brix value of the validation set). Further, as shown in FIG. 8B, a majority of the residuals between the predicted Brix values and the lab Brix values for the validation set by the transferred calibration model stayed within ±2RMSEP of the original FOSS master calibration model. Notably, the fLMC technique is the only technique that can be used in a case where master calibration set is unavailable, grids differ between the master instrument and the target instrument, only a scouting set collected by the target instrument for transfer, and there are no reference values for the scouting set. In some implementations, the performance of the transferred calibration model may be further improved with calibration model updating.

As indicated above, FIGS. 7A-7C and 8A and 8B are provided merely as examples. Other examples are possible and may differ from what was described with regard to FIGS. 7A-7C and FIGS. 8A and 8B.

In some implementations, the techniques described herein may be used in order to achieve standardization of calibration models across multiple instruments. As described above, instrument-to-instrument variations are commonly encountered for the same type of instruments or devices. Thus, when a calibration model is developed on one instrument but needs to be deployed on multiple (e.g., hundreds, millions, and/or the like) of instruments, instrument-to-instrument variations may cause inconsistent performance. It may not be practical to perform calibration model transfer using typical methods for this problem, especially when the instruments are at various locations. The LMC technique and the fLMC technique can be configured on the instruments in order to solve this problem. Here, when a master calibration model is delivered to a target instrument, spectra from only a few samples need to be collected. The calibration model can be corrected automatically using the LMC technique (e.g., when reference values for the scouting set are available) or the fLMC technique (e.g., regardless of whether reference values for the scouting set are available).

Figure 9A:
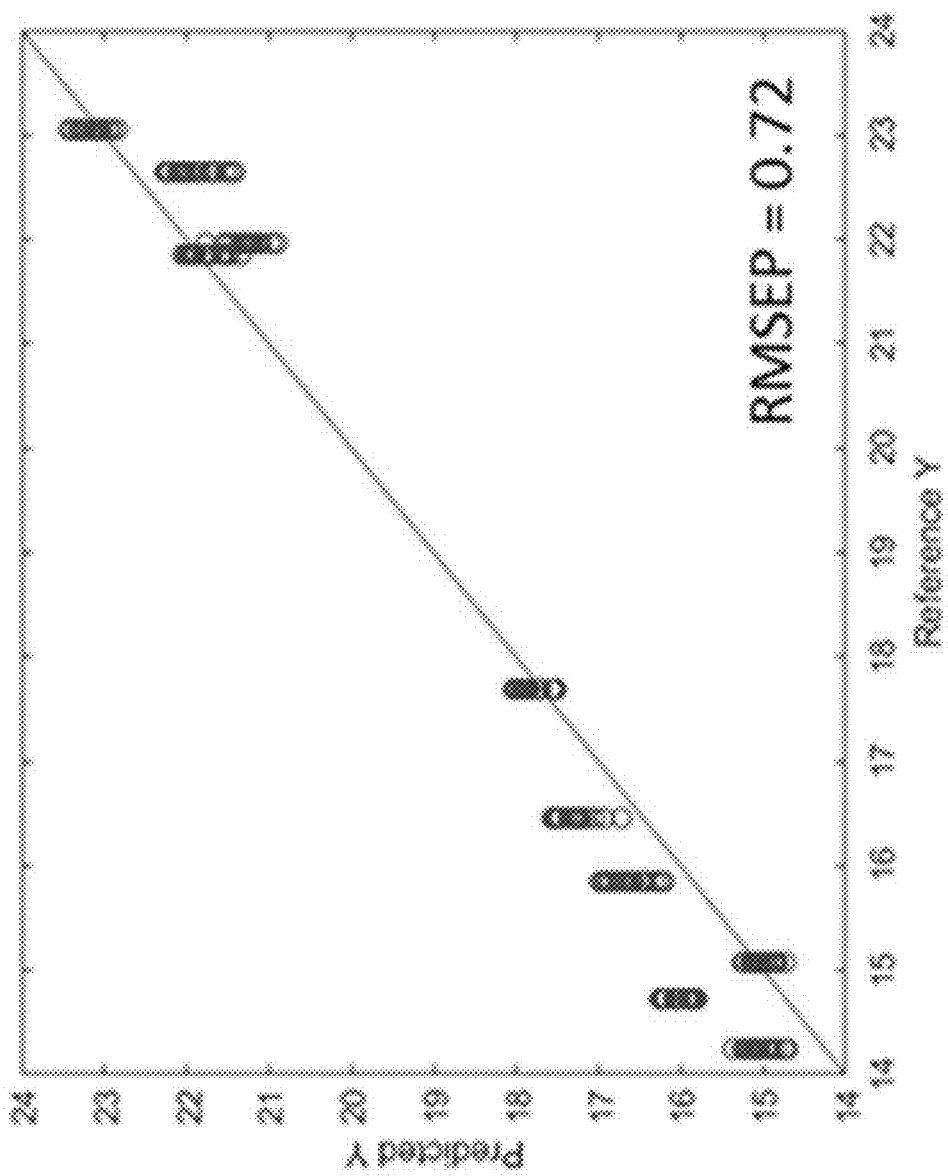
Figure 9B:
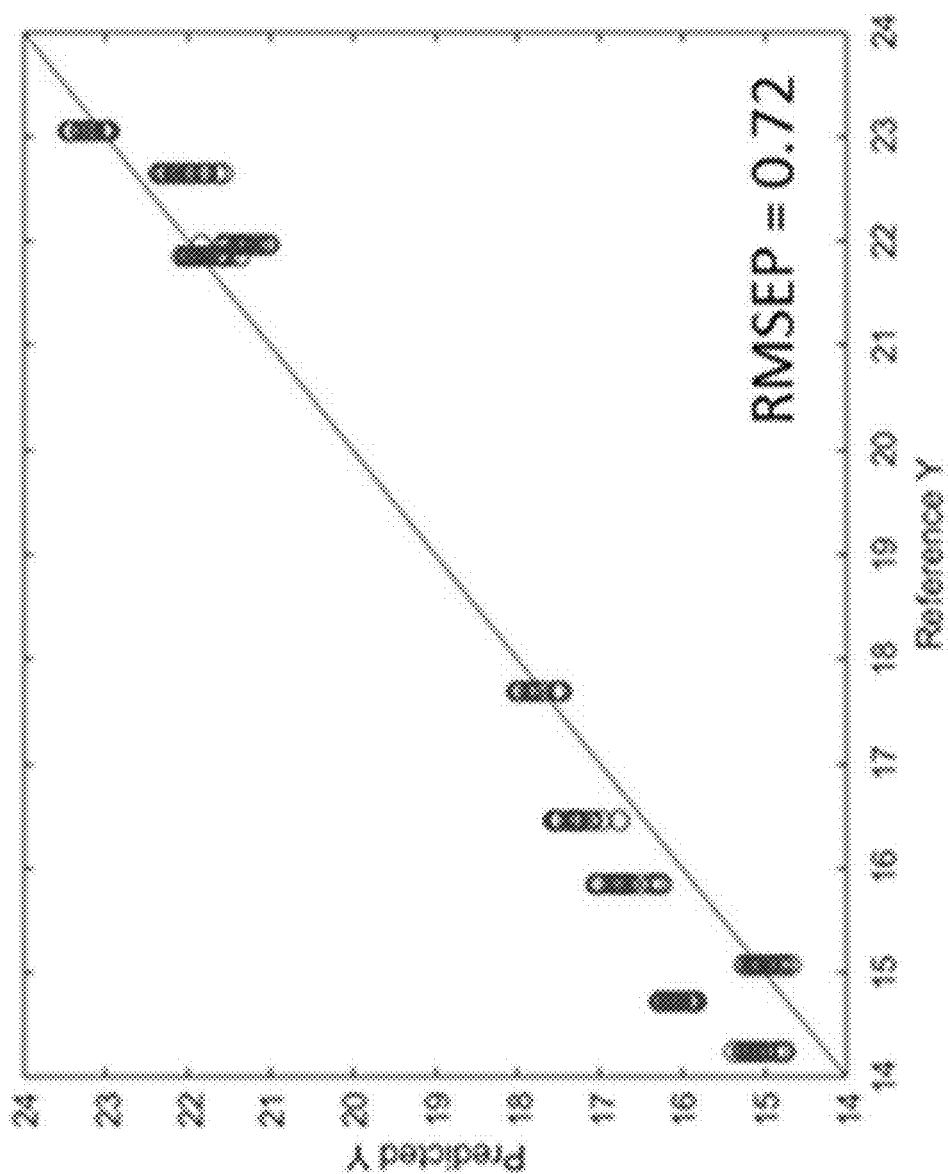
Figure 9C:
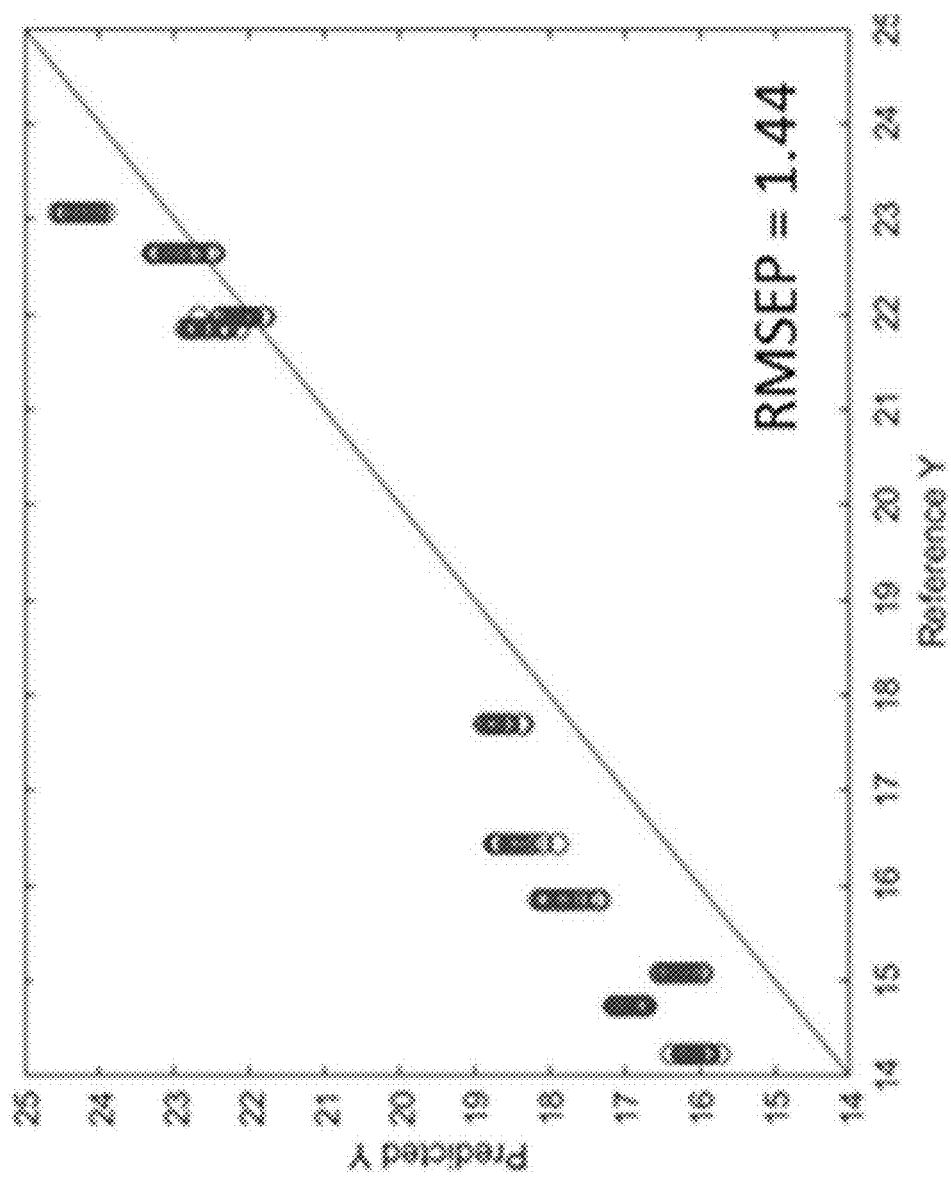
Figure 9D:
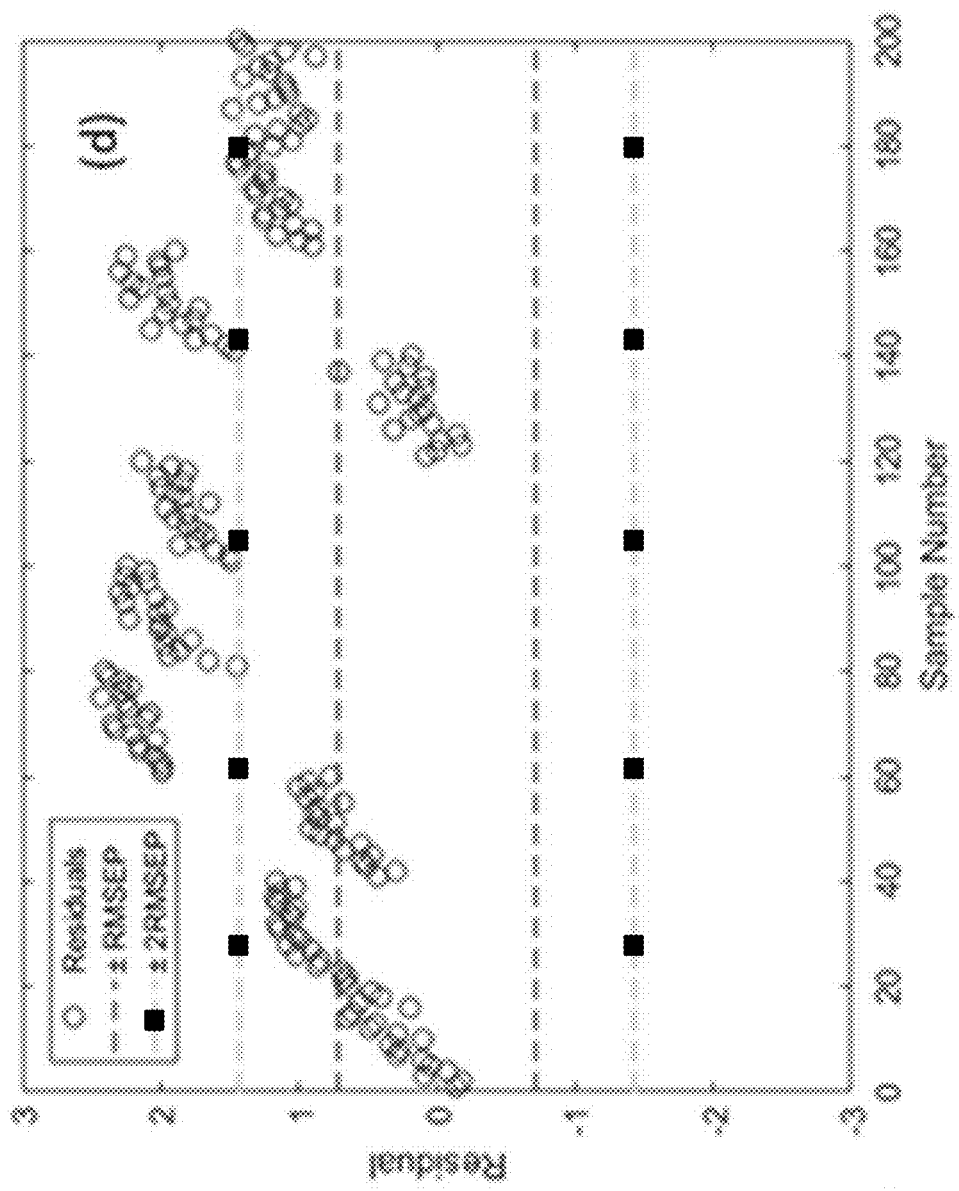

FIGS. 9A-9D, 10A, 10B, 11A, and 11B are diagrams illustrating example results associated with achieving standardization of a calibration model across multiple instruments. In the example associated with FIGS. 9A-9D, 10A, 10B, 11A, and 11B, raw data from a MicroNIR device were calibrated in two different ways (Data A and Data B) to simulate instrument-to-instrument variations. 759 spectra from 38 mixture samples were used to build a calibration model to predict caffeine content. 200 spectra from the other 10 mixture samples were used as a validation set. As shown in FIGS. 9A and 9B, when using calibration model A to predict validation data A, or when using calibration model B to predict validation data B, the performance was similar. However, as shown in FIG. 9C, when using calibration model A to predict validation data B, the performance was deteriorated. As shown in FIG. 9D, many residuals between the predicted values and the lab values for the validation set B were out of the ±2RMSEP benchmarks of using model A to predict validation A.

Figure 11A:
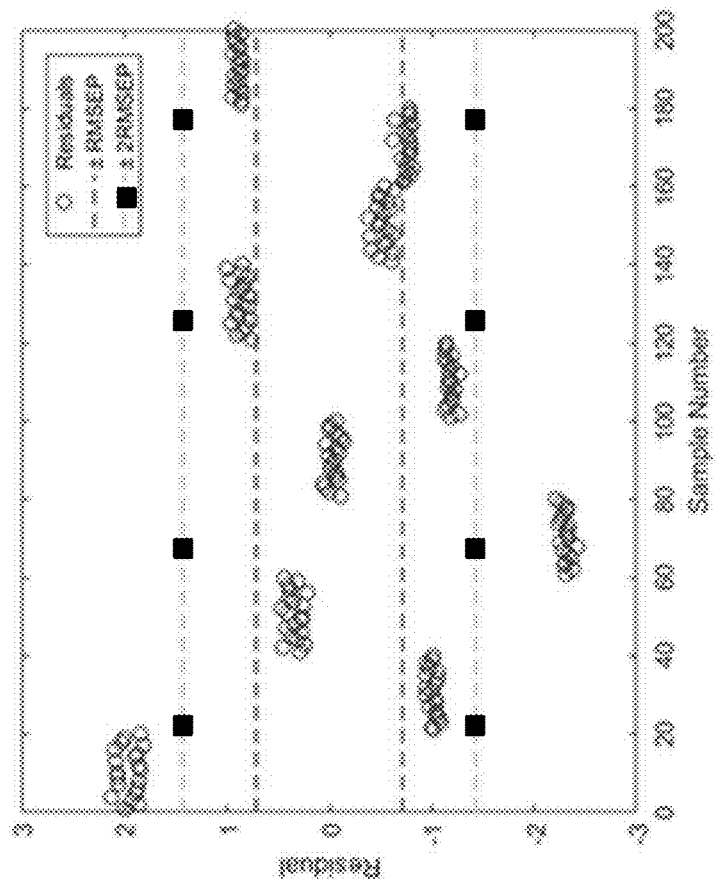
Figure 11B:
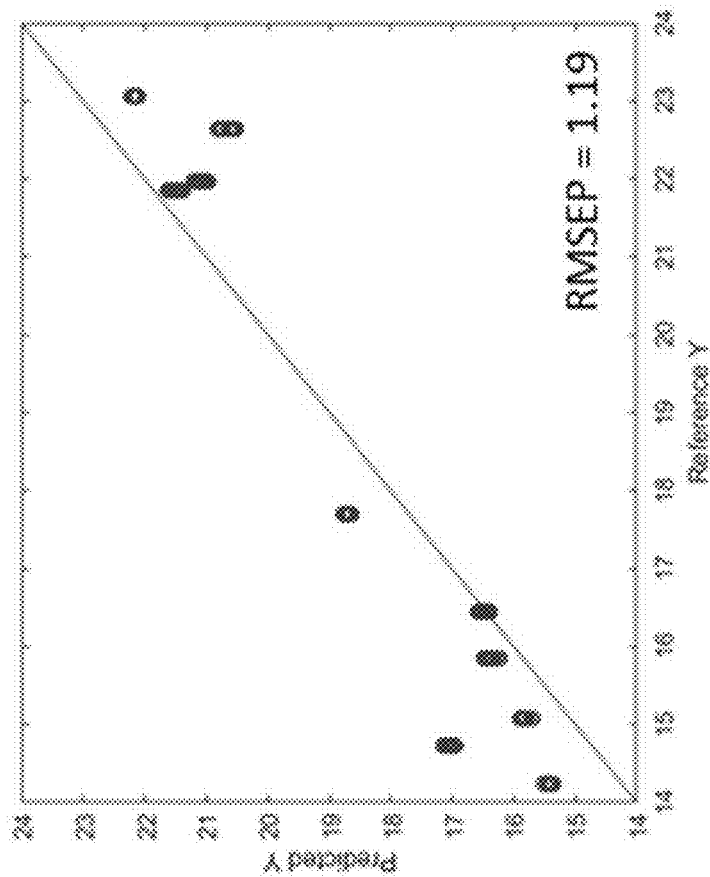

Ten samples with three replicated spectra were randomly selected from the calibration set B as the scouting set to perform the LMC technique and the fLMC technique. As shown in FIG. 10A, with the LMC technique, RMSEP was significantly reduced. As shown in FIG. 10B, all the prediction residuals were within the ±2RMSEP benchmarks of using model A to predict validation A. As shown in FIG. 11A, with the fLMC technique, RMSEP was similarly reduced. As shown in FIG. 11B, most of the prediction residuals were within the ±2RMSEP benchmarks of using model A to predict validation A. Hence, it is effective to use the LMC technique or the fLMC technique to correct for instrument-to-instrument differences in model performance.

In fact, when as few as 8 samples were used as the scouting set, the LMC technique and the fLMC technique are effective. Notably, the results in FIGS. 10A, 10B, 11A and 11B are examples of medium performance. The scouting samples were selected randomly to simulate the real testing scenario on the user side. Final performance results were impacted by which samples were used as the scouting set. Again, the fLMC technique did not perform as well as the LMC technique. However, when there are no reference values available for the scouting set, the fLMC technique is the only technique that can be used for calibration model transfer.

As indicated above, FIGS. 9A-9D, 10A, 10B, 11A, and 11B are provided merely as examples. Other examples are possible and may differ from what was described with regard to FIGS. 9A-9D, 10A, 10B, 11A, and 11B.

As described above, in some cases, the LMC technique can be applied to calibration model updating by using updating samples as a scouting set for the LMC technique. Notably, this does not require the use of all the calibration data (e.g., as required by a typical model updating technique that adds the updating samples to the calibration set and recalibrates the model), and takes a relatively short amount time such that calibration model updating can be performed during online operation of an instrument (e.g., master instrument 205, target instrument 210).

Figure 12:
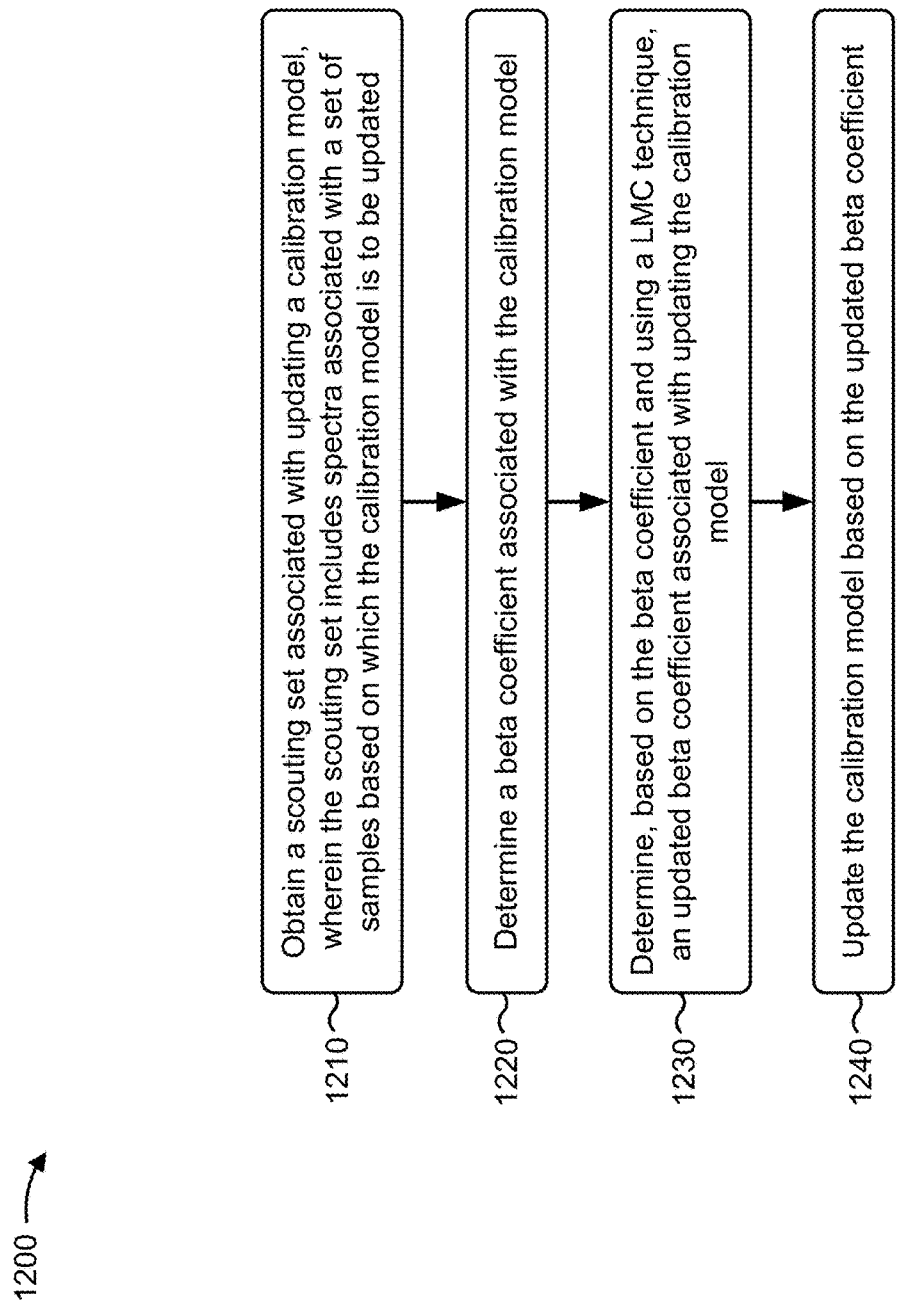
FIG. 12 is a flow chart of an example process for model updating using a linear model correction technique, as described herein.

FIG. 12 is a flow chart of an example process 1200 for using the LMC technique in order to perform calibration model updating. In some implementations, one or more process blocks of FIG. 12 may be performed by modeling device 215. In some implementations, one or more process blocks of FIG. 12 may be performed by another device or a group of devices separate from or including modeling device 215, such as master instrument 205 and/or target instrument 210.

As shown in FIG. 12, process 1200 may include obtaining a scouting set associated with updating a calibration model, wherein the scouting set includes spectra associated with a set of samples based on which the calibration model is to be updated (block 1210). For example, modeling device 215 may obtain a scouting set associated with updating a calibration model, wherein the scouting set includes spectra associated with a set of samples based on which the calibration model is to be updated.

As further shown in FIG. 12, process 1200 may determining, a beta coefficient associated with the calibration model (block 1220). For example, modeling device 215 may determine a beta coefficient associated with the calibration model.

As further shown in FIG. 12, process 1200 may include determining, based on the beta coefficient and using a LMC technique, an updated beta coefficient associated with updating the calibration model (block 1230). For example, modeling device 215 may determine, based on the beta coefficient and using a LMC technique, an updated beta coefficient associated with updating the calibration model.

As further shown in FIG. 12, process 1200 may include updating the calibration model based on the updated beta coefficient (block 1240). For example, modeling device 215 may update the calibration model based on the updated beta coefficient (e.g., such that the updated calibration model uses the updated beta coefficient in association with performing calibration).

Process 1200 may include additional implementations, such as any single implementation or any combination of implementations described below and/or in connection with one or more other processes described elsewhere herein.

In some implementations, the updating of the calibration model is performed during operation of the instrument (e.g., master instrument 205, target instrument 210) without taking the device offline.

Although FIG. 12 shows example blocks of process 1200, in some implementations, process 1200 may include additional blocks, fewer blocks, different blocks, or differently arranged blocks than those depicted in FIG. 12. Additionally, or alternatively, two or more of the blocks of process 1200 may be performed in parallel.

Figures 13A, 13B:
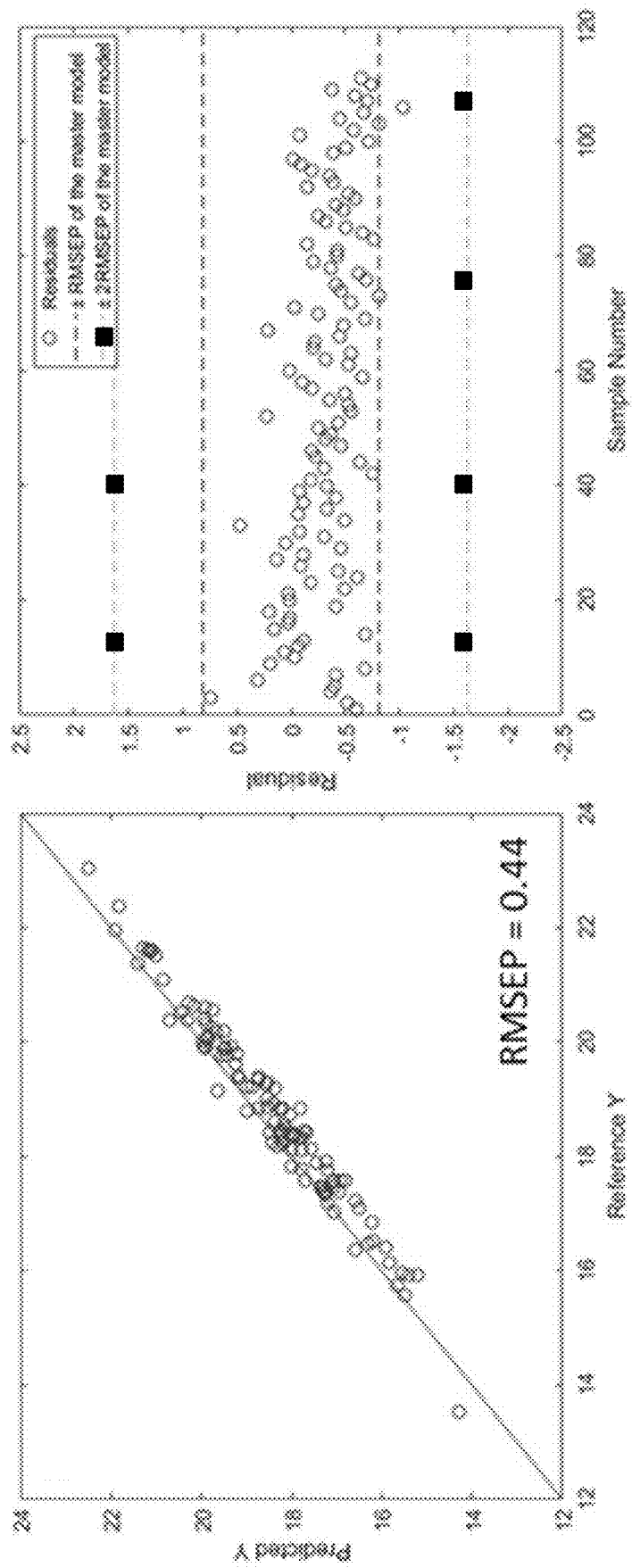
FIGS. 13A and 13B are diagrams illustrating example results of performing calibration model updating using a linear model correction technique.

FIGS. 13A and 13B are diagrams illustrating example results of performing calibration model updating using a linear model correction technique.

In order to update the Brix model (described above in association with FIG. 7B) for sugarcane, an additional 30 MicroNIR spectra were used as the updating set. Here, the LMC technique was applied to update the calibration model. FIG. 13A is a diagram that shows prediction results associated with this update, for the same validation set as used in FIG. 7B. As shown, the model performance was improved, with reduced RMSEP and reduced prediction residuals, as shown in FIG. 13B.

As indicated above, FIGS. 13A and 13B are provided merely as examples. Other examples are possible and may differ from what was described with regard to FIGS. 13A and 13B.

As described above, the LMC technique requires reference values for the scouting set. When transfer sets from both master instrument 205 and target instrument 210 are available, but reference values for these samples are unavailable, the reference values can be predicted using a master calibration model and a master transfer set in order to make the LMC technique usable.

Figure 14B:
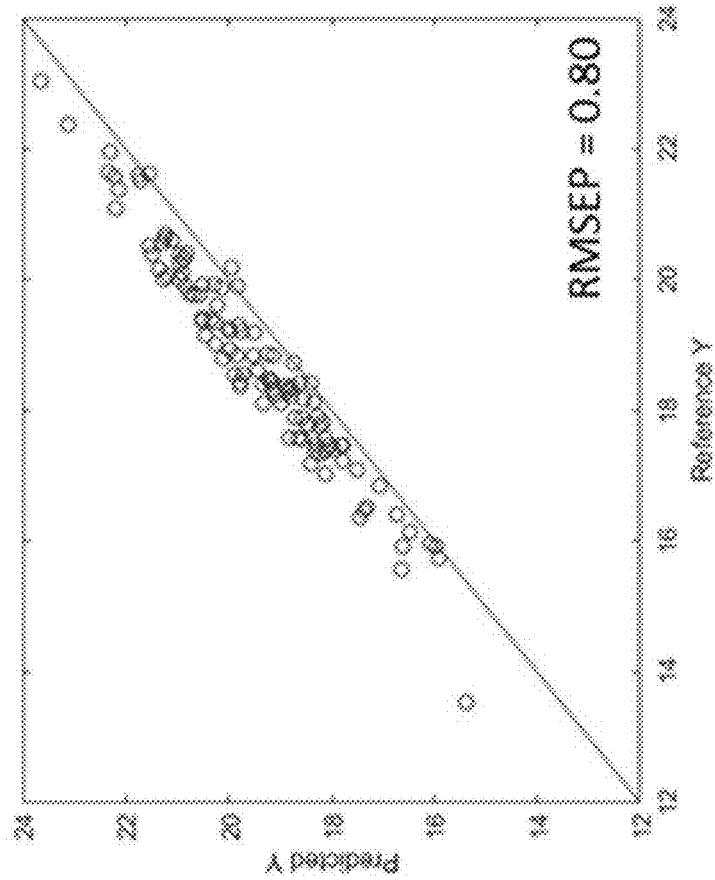
FIGS. 14A and 14B are diagrams illustrating example results associated with predicting reference values using a master calibration model and a master transfer set.
Figure 14A:
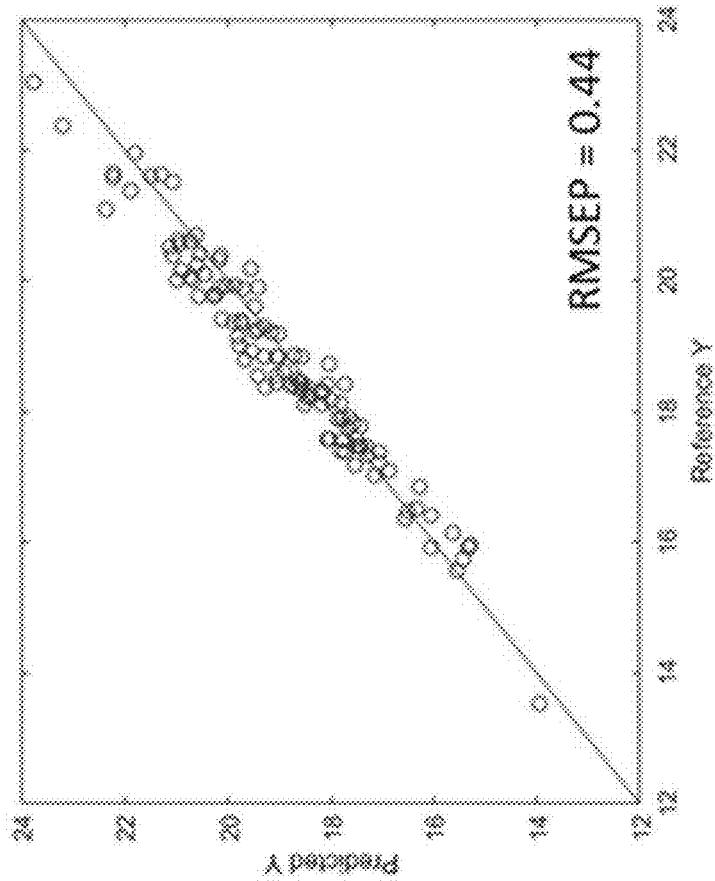

FIGS. 14A and 14B are diagrams illustrating example results associated with predicting reference values using a master calibration model and a master transfer set. As shown in FIG. 14A, using the same data sets as those associated with FIGS. 5A-5C, RMSEP was 0.44 when the true reference values were used. As shown by FIG. 14B, the RMSEP was 0.80 when using reference values predicted using the master calibration model and the master transfer set. Although performance of the LMC technique performance using the predicted reference values was not as good as performing the LMC technique using the true reference values, the performance was improved as compared to using the MDC technique or the fLMC technique, and similar to using the PDS technique, as described above.

As indicated above, FIGS. 14A and 14B are provided merely as examples. Other examples are possible and may differ from what was described with regard to FIGS. 14A and 14B.

Some implementations described herein provide a focused LMC (fLMC) technique that can be used in association with performing calibration model transfer. Similar to the LMC technique, the fLMC technique requires only a scouting set collected by the target instrument. However, unlike the LMC technique, the fLMC technique does not require reference values for the scouting set. As such, use of the fLMC technique in association with calibration model transfer reduces cost, difficulty, and/or complexity of calibration model transfer (e.g., as compared to the LMC technique, as well as typical calibration model transfer techniques described above).

Some implementations described herein provide a procedure in which the fLMC technique or the LMC technique uses beta coefficients of a master calibration model in association with performing a calibration model transfer, without a need for the master calibration set.

Some implementations described herein provide a procedure for model updating using the LMC technique.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
   determining, by one or more devices, whether a grid of a master instrument matches a grid of a target instrument;
   identifying, by the one or more devices, a master beta coefficient based on determining whether the grid of the master instrument matches the grid of the target instrument and based on one of:
      a beta coefficient of a master calibration model, or
      a master calibration set associated with the master calibration model;
   generating, by the one or more devices, an initial pair of transferred beta coefficients based on the master beta coefficient;
   generating, by the one or more devices and using a focused linear model correction (fLMC) technique, a transferred calibration model based on the initial pair of transferred beta coefficients; and
   providing, by the one or more devices, the transferred calibration model to the target instrument.

2. The method of claim 1, wherein generating the initial pair of transferred beta coefficients comprises:
   generating the initial pair of transferred beta coefficients by one or more of:
      applying a linear function, associated with a random value, to the master beta coefficient, or
      adding a random value to the master beta coefficient.

3. The method of claim 1, wherein determining whether the grid of the master instrument matches the grid of the target instrument comprises:
   determining whether the grid of the master instrument matches the grid of the target instrument based on information provided by one or more of the master instrument or the target instrument.

4. The method of claim 1, wherein determining whether the grid of the master instrument matches the grid of the target instrument comprises:
   determining that the grid of the master instrument matches the grid of the target instrument, and
   wherein identifying the master beta coefficient comprises:

identifying the beta coefficient of the master calibration model as the master beta coefficient based on determining that the grid of the master instrument matches the grid of the target instrument.

5. The method of claim 1, wherein the transferred calibration model is generated without using reference values for a scouting set.

6. The method of claim 1, wherein, when the grid of the master instrument matches the grid of the target instrument, the beta coefficient of the master calibration model is identified as the master beta coefficient irrespective of whether the master calibration set, associated with the master calibration model, is available.

7. The method of claim 1,
wherein the master instrument is a benchtop near infrared (NIR) master instrument, and wherein the target instrument is a portable MicroNIR target instrument.

8. A device, comprising:
one or more memories; and
one or more processors, communicatively coupled to the one or more memories, configured to:
determine whether a grid of a master instrument matches a grid of a target instrument;
identify a master beta coefficient based on determining whether the grid of the master instrument matches the grid of the target instrument and based on one of:
a beta coefficient of a master calibration model, or
a master calibration set associated with the master calibration model;
generate an initial pair of transferred beta coefficients based on the master beta coefficient;
generate, using a focused linear model correction (fLMC) technique, a transferred calibration model based on the initial pair of transferred beta coefficients; and
provide the transferred calibration model to the target instrument.

9. The device of claim 8, wherein the one or more processors, when generating the initial pair of transferred beta coefficients, are configured to:
generate the initial pair of transferred beta coefficients by one or more of:
apply a linear function, associated with a random value, to the master beta coefficient, or
add a random value to the master beta coefficient.

10. The device of claim 8, wherein the one or more processors, when determining whether the grid of the master instrument matches the grid of the target instrument, are configured to:
determine whether the grid of the master instrument matches the grid of the target instrument based on information provided by one or more of the master instrument or the target instrument.

11. The device of claim 8, wherein the one or more processors, when determining whether the grid of the master instrument matches the grid of the target instrument, are configured to:
determine that the grid of the master instrument matches the grid of the target instrument, and
wherein the one or more processors, when identifying the master beta coefficient, are configured to:
identify the beta coefficient of the master calibration model as the master beta coefficient based on determining that the grid of the master instrument matches the grid of the target instrument.

12. The device of claim 8, wherein the transferred calibration model is generated without using reference values for a scouting set.

13. The device of claim 8, wherein, when the grid of the master instrument matches the grid of the target instrument, the beta coefficient of the master calibration model is identified as the master beta coefficient irrespective of whether the master calibration set, associated with the master calibration model, is available.

14. The device of claim 8,
wherein the master instrument is a benchtop near infrared (NIR) master instrument, and wherein the target instrument is a portable MicroNIR target instrument.

15. A non-transitory computer-readable medium storing a set of instructions, the set of instructions comprising:
one or more instructions that, when executed by one or more processors of one or more devices, cause the one or more devices to:
determine whether a grid of a master instrument matches a grid of a target instrument;
identify a master beta coefficient based on determining whether the grid of the master instrument matches the grid of the target instrument and based on one of:
a beta coefficient of a master calibration model, or
a master calibration set associated with the master calibration model;
generate an initial pair of transferred beta coefficients based on the master beta coefficient;
generate, using a focused linear model correction (fLMC) technique, a transferred calibration model based on the initial pair of transferred beta coefficients; and
provide the transferred calibration model to the target instrument.

16. The non-transitory computer-readable medium of claim 15, wherein the one or more instructions, that cause the one or more devices to generate the initial pair of transferred beta coefficients, cause the one or more devices to:
generate the initial pair of transferred beta coefficients by one or more of:
apply a linear function, associated with a random value, to the master beta coefficient, or
add a random value to the master beta coefficient.

17. The non-transitory computer-readable medium of claim 15, wherein the one or more instructions, that cause the one or more devices to determine whether the grid of the master instrument matches the grid of the target instrument, cause the one or more devices to:
determine whether the grid of the master instrument matches the grid of the target instrument based on information provided by one or more of the master instrument or the target instrument.

18. The non-transitory computer-readable medium of claim 15, wherein the one or more instructions, that cause the one or more devices to determine whether the grid of the master instrument matches the grid of the target instrument, cause the one or more devices to:
determine that the grid of the master instrument matches the grid of the target instrument, and
wherein the one or more instructions, that cause the one or more devices to identify the master beta coefficient, cause the one or more devices to:
identify the beta coefficient of the master calibration model as the master beta coefficient based on determining that the grid of the master instrument matches the grid of the target instrument.

19. The non-transitory computer-readable medium of claim 15, wherein the transferred calibration model is generated without using reference values for a scouting set.

20. The non-transitory computer-readable medium of claim 15, wherein, when the grid of the master instrument matches the grid of the target instrument, the beta coefficient of the master calibration model is identified as the master beta coefficient irrespective of whether the master calibration set, associated with the master calibration model, is available.

* * * * *